(12) United States Patent
Poupot et al.

(10) Patent No.: US 11,186,634 B2
(45) Date of Patent: Nov. 30, 2021

(54) ANTIBODIES TARGETING TUMOR ASSOCIATED MACROPHAGES AND USES THEREOF

(71) Applicants: INSERM (Institut National de la Sante et de la Recherche Medicale), Paris (FR); Universite Paul Sabatier Toulouse III, Toulouse (FR); Centre National de la Recherche Scientifique (CNRS), Paris (FR); Centre Hospitalier Universitaire de Toulouse, Toulouse (FR); Institut Claudius Regaud, Toulouse (FR)

(72) Inventors: Mary Poupot, Toulouse (FR); Loïc Ysebaert, Toulouse (FR); Marie Tosolini, Toulouse (FR); Jean-Jacques Fournie, Toulouse (FR); Pierre Brousset, Toulouse (FR); Philippe Rochaix, Toulouse (FR)

(73) Assignees: INSERM (Institut National de la Santé et de la Recherche Médicale), Paris (FR); Université Paul Sabatier Toulouse, Toulouse (FR); Centre National de la Recherche Scientifique (CNRS), Paris (FR); Centre Hospitalier Universitaire de Toulouse, Toulouse (FR); Institut Claudius Regaud, Toulouse (FR)

( * ) Notice: Subject to any disclaimer, the term of this patent is extended or adjusted under 35 U.S.C. 154(b) by 470 days.

(21) Appl. No.: 16/319,956

(22) PCT Filed: Jul. 28, 2017

(86) PCT No.: PCT/EP2017/069174
§ 371 (c)(1),
(2) Date: Jan. 23, 2019

(87) PCT Pub. No.: WO2018/020000
PCT Pub. Date: Feb. 1, 2018

(65) Prior Publication Data
US 2021/0292408 A1    Sep. 23, 2021

(30) Foreign Application Priority Data

Jul. 29, 2016   (EP) .................................... 16305992

(51) Int. Cl.
| C07K 16/28 | (2006.01) |
| G01N 33/50 | (2006.01) |
| C12N 5/09 | (2010.01) |
| C12Q 1/6886 | (2018.01) |
| G01N 33/574 | (2006.01) |

(52) U.S. Cl.
CPC .......... *C07K 16/28* (2013.01); *G01N 33/574* (2013.01); *C07K 2317/24* (2013.01); *C07K 2317/565* (2013.01); *C07K 2317/70* (2013.01)

(58) Field of Classification Search
None
See application file for complete search history.

(56) References Cited

FOREIGN PATENT DOCUMENTS

WO    2016/077837 A1    5/2016

OTHER PUBLICATIONS

Murase et al., Serum autoantibody to sideroflexin 3 as a novel tumor marker for oral squamous cell carcinoma. Proteomics vol. 2, Issue4 No. 4 Apr. 2008, pp. 517-527. (Year: 2008).*
(Continued)

*Primary Examiner* — Aurora M Fontainhas
(74) *Attorney, Agent, or Firm* — W&C IP

(57) ABSTRACT

The present invention relates to antibodies targeting Tumor Associated Macrophages (TAMs) and uses thereof. The inventors investigated specific marker exposed on the sur-
(Continued)

Figure 1A:
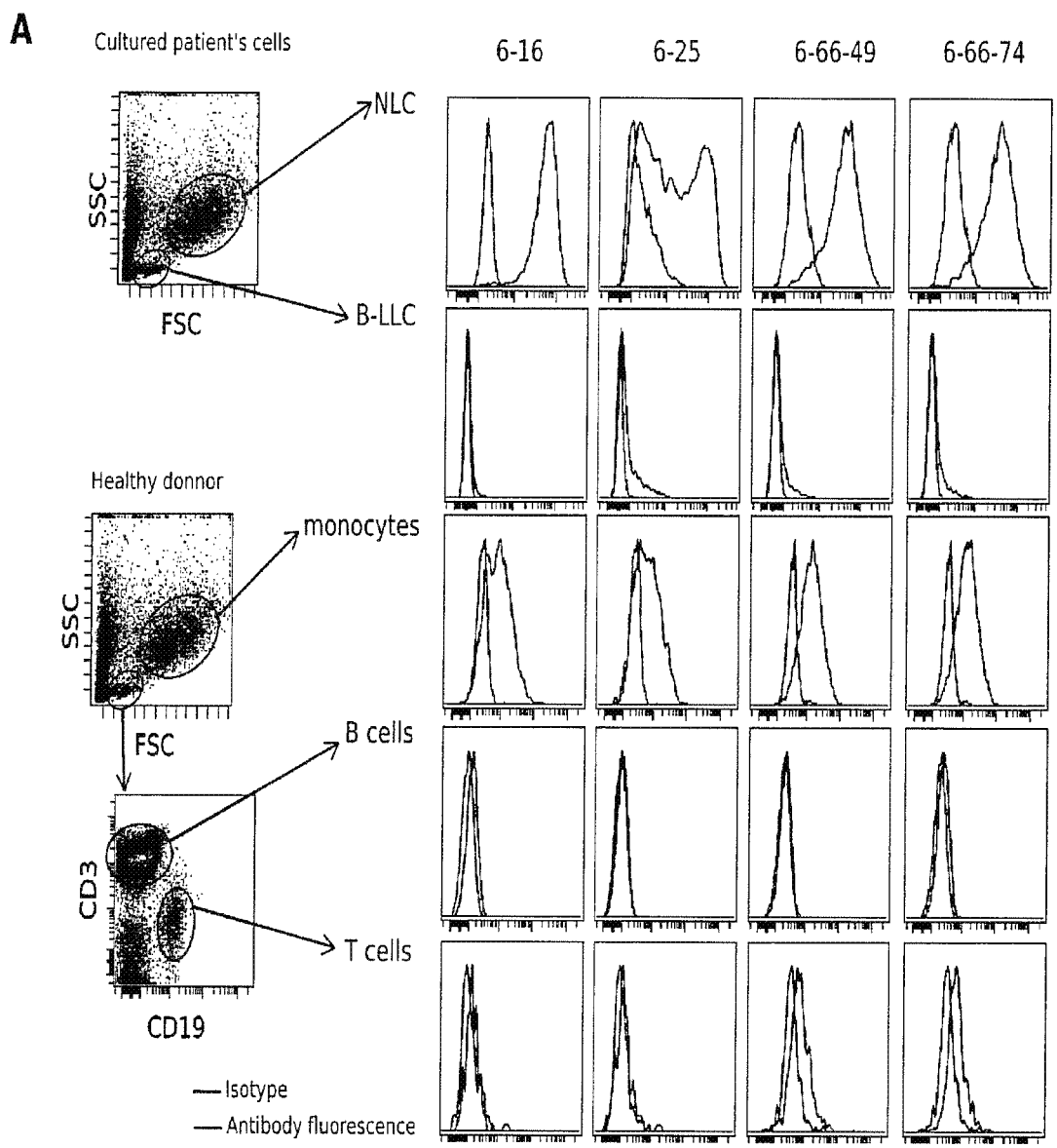

face of the macrophages associated to tumor in order to detect and target TAMs. They showed that sideroflexin 3, which is absent in normal macrophage, is expressed by tumor associated macrophages. The inventors further demonstrated that using antibody directed to sideroflexin 3, they depleted TAMs in PBMC sample obtained from LCC patient, and strongly reduced leukemic B cells number.

17 Claims, 8 Drawing Sheets

Specification includes a Sequence Listing.

(56) References Cited

OTHER PUBLICATIONS

Database Geneseq (Online); "Humanized anti-GPVI antibody heavy chain variable region SEQ:12"; retrieved from EGI accession No. GSP:AZJ30625; Database accession No. AZJ30625 sequence.
Cassier et al.; "CSFIR inhibition with emactuzumab in locally advanced diffuse-type tenosynovial giant cell tumours of the soft tissue: a dose-escalation and dose-expansion phase 1 study"; The Lancet, Oncology, Aug. 1, 2015, pp. 949-956.
Murase et al.; "Serum autoantibody to sideroflexin 3 as a novel tumor marker for oral squamous cell carcinoma"; Proteomics—Clinical Applications, vol. 2, No. 4, Apr. 1, 2008, pp. 517-527.

* cited by examiner

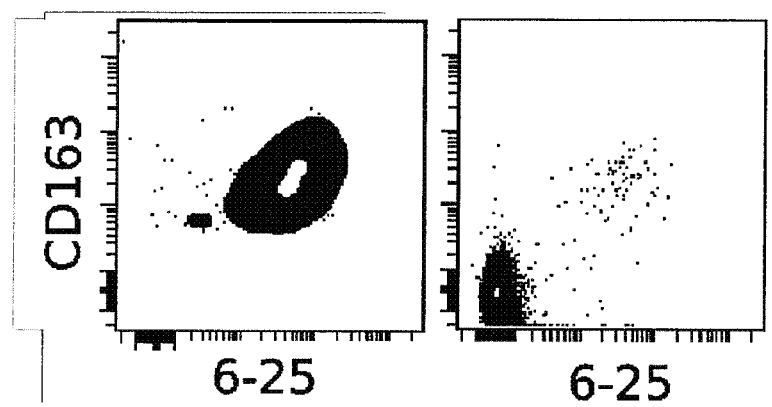
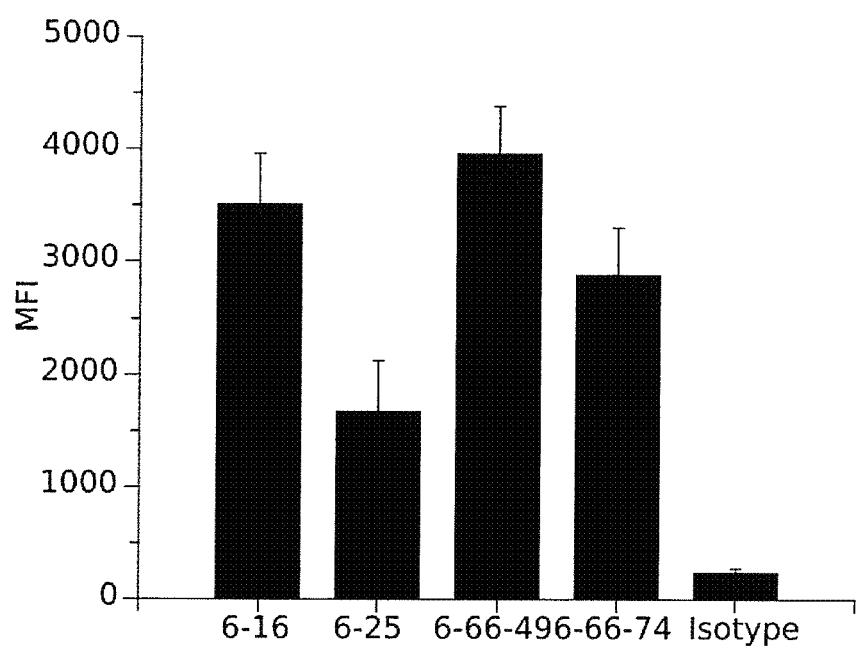
Figure 1 B and C

```
                         SEQUENCE LISTING

<160> NUMBER OF SEQ ID NOS: 16

<210> SEQ ID NO 1
    <211> LENGTH: 8
    <212> TYPE: PRT
    <213> ORGANISM: Artificial Sequence
    <220> FEATURE:
    <223> OTHER INFORMATION: Synthetic H-CDR1

<400> SEQUENCE: 1

Gly Phe Ser Leu Thr Gly Tyr Gly
    1               5

<210> SEQ ID NO 2
    <211> LENGTH: 7
    <212> TYPE: PRT
    <213> ORGANISM: Artificial Sequence
    <220> FEATURE:
    <223> OTHER INFORMATION: Synthetic H-CDR2

<400> SEQUENCE: 2

Ile Trp Gly Asp Gly Ser Thr
    1               5

<210> SEQ ID NO 3
    <211> LENGTH: 9
    <212> TYPE: PRT
    <213> ORGANISM: Artificial Sequence
    <220> FEATURE:
    <223> OTHER INFORMATION: Synthetic H-CDR3

<400> SEQUENCE: 3

Ala Arg Asp Leu Lys Phe Ala Tyr Trp
```

-continued

```
<210> SEQ ID NO 4
<211> LENGTH: 6
<212> TYPE: PRT
<213> ORGANISM: Artificial Sequence
<220> FEATURE:
<223> OTHER INFORMATION: Synthetic L-CDR1

<400> SEQUENCE: 4

Gln His Val Thr Thr Ala
1               5

<210> SEQ ID NO 5
<211> LENGTH: 3
<212> TYPE: PRT
<213> ORGANISM: Artificial
<220> FEATURE:
<223> OTHER INFORMATION: Synthetic L-CDR2

<400> SEQUENCE: 5

Ser Ala Ser
1

<210> SEQ ID NO 6
<211> LENGTH: 9
<212> TYPE: PRT
<213> ORGANISM: Artificial Sequence
<220> FEATURE:
<223> OTHER INFORMATION: Synthetic L-CDR3

<400> SEQUENCE: 6

Gln Gln His Tyr Thr Thr Pro Trp Thr
1               5

<210> SEQ ID NO 7
<211> LENGTH: 114
<212> TYPE: PRT
<213> ORGANISM: Artificial Sequence
<220> FEATURE:
<223> OTHER INFORMATION: Synthetic H-VD

<400> SEQUENCE: 7

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Gly Tyr
            20                  25                  30

Gly Val Asn Trp Val Arg Gln Pro Pro Gly Lys Gly Leu Glu Trp Leu
        35                  40                  45

Gly Met Ile Trp Gly Asp Gly Ser Thr Asp Tyr Asn Ser Asp Leu Lys
    50                  55                  60

Ser Arg Leu Ser Ile Thr Glu Asp Asn Ser Lys Arg Gln Val Phe Leu
65                  70                  75                  80

Lys Met Asp Ser Leu Gln Thr Glu Asp Thr Ala Arg Tyr Tyr Cys Ala
                85                  90                  95

Arg Asp Leu Lys Phe Ala Tyr Trp Gly Gln Gly Thr Leu Val Thr Val
            100                 105                 110

Ser Ala

<210> SEQ ID NO 8
<211> LENGTH: 107
<212> TYPE: PRT
<213> ORGANISM: Artificial Sequence
```

-continued

<220> FEATURE:
<223> OTHER INFORMATION: Synthetic L-VD

<400> SEQUENCE: 8

Asp Ile Val Met Thr Gln Ser His Lys Phe Met Ser Ser Val Gly
1               5                   10                  15

Asp Arg Val Ser Ile Thr Cys Lys Ala Ser Gln His Val Thr Ala
            20                  25                  30

Val Ala Trp Phe Gln Gln Lys Pro Gly Gln Ser Pro Lys Leu Leu Ile
        35                  40                  45

Tyr Ser Ala Ser Phe Arg Tyr Thr Gly Val Pro Asp Arg Phe Thr Gly
    50                  55                  60

Ser Gly Ser Gly Thr Asp Phe Thr Phe Thr Ile Ser Thr Val Gln Ala
65                  70                  75                  80

Glu Asp Leu Ala Val Tyr Tyr Cys Gln Gln His Tyr Thr Thr Pro Trp
                85                  90                  95

Thr Phe Gly Gly Gly Thr Lys Leu Glu Ile Lys
            100                 105

<210> SEQ ID NO 9
<211> LENGTH: 340
<212> TYPE: DNA
<213> ORGANISM: Artificial Sequence
<220> FEATURE:
<223> OTHER INFORMATION: Synthetic H-VD nucleic acid sequence

<400> SEQUENCE: 9
caggtgcagc tgaaggagtc aggacctggc ctggtggcgc cctcacagag cctgtccatc      60
acatgcaccg tctcagggtt ctcattaacc ggctatggtg taaactgggt tcgccagcct    120
ccaggaaggg tctggagtgg ctgggaatga tatggggtga tggaagcaca gactataatt    180
cagatctcaa atccagactg agcatcaccg aggacaactc caagcgccaa gttttcttaa    240
aaatggacag tctgaaactg aagacacagc caggtactac tgtgccagag atcttaagtt    300
tgcttactgg ggccaaggga ctctggtcac tgtctctgca                          340

<210> SEQ ID NO 10
<211> LENGTH: 319
<212> TYPE: DNA
<213> ORGANISM: Artificial Sequence
<220> FEATURE:
<223> OTHER INFORMATION: Synthetic L-VD nucleic acid sequence

<400> SEQUENCE: 10
gacattgtga tgacccagtc tcacaaattc atgtcctcat cagtaggaga cagggtcagc      60
atcacctgca aggccagtca acatgtgact actgctgttg cctggtttca acagaaacca    120
ggacaattcc taaactactg atttactcgg catccttccg gtacactgga gtccctgatc    180
gcttcactgg cagtggatct gggacggatt tcactttcac catcagcact gtgcaggctg    240
aagacctggc agttattact gtcagcaaca ttatactact ccgtggacgt tcggtggagg    300
caccaagctg gaaatcaaa                                                  319

<210> SEQ ID NO 11
<211> LENGTH: 7
<212> TYPE: PRT
<213> ORGANISM: Artificial Sequence
<220> FEATURE:
<223> OTHER INFORMATION: Synthetic H-CDR1 Kabat system

<400> SEQUENCE: 11

```
Gly Phe Ser Leu Thr Gly Tyr
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic H-CDR2 Kabat system

<400> SEQUENCE: 12

Trp Gly Asp Gly Ser
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic H-CDR3 Kabat system

<400> SEQUENCE: 13

Asp Leu Lys Phe Ala Tyr
1               5

<210> SEQ ID NO 14
<211> LENGTH: 11
<212> TYPE: PRT
<213> ORGANISM: Artificial Sequence
<220> FEATURE:
<223> OTHER INFORMATION: Synthetic L-CDR1 Kabat system

<400> SEQUENCE: 14

Lys Ala Ser Gln His Val Thr Thr Ala Val Ala
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Synthetic L-CDR2 Kabat system

<400> SEQUENCE: 15

Ser Ala Ser Phe Arg Tyr Thr
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic L-CDR3 Kabat system

<400> SEQUENCE: 16

Gln Gln His Tyr Thr Thr Pro Trp Thr
1               5
```

ANTIBODIES TARGETING TUMOR ASSOCIATED MACROPHAGES AND USES THEREOF

FIELD OF THE INVENTION

The present invention relates to antibodies targeting Tumor Associated Macrophages (TAMs) and uses thereof.

BACKGROUND OF THE INVENTION

The importance of the tumor microenvironment in promoting cancer initiation and tumor growth has been increasingly recognized over the past decade (H. Korkaya JCI, 121, (10), 3804-3809, 2011; E. Lonardo, J. Frias-Aldeguer, Cell Cycle, 11(7), 1282-1290, 2012; J. W. Pollard, Nature Reviews Immunology, 9 (4), 259-270, 2009).

The tumor microenvironment is characterized by chronic inflammation, which, instead of inhibiting tumor growth, favors tumor formation by stimulating cell proliferation, activating Cancer stem cells (CSCs), and promoting metastasis [V. Plaks, Cell Stem Cell, 16(3), 225-238, 2015; S. M. Cabarcas, L. A. International Journal of Cancer, 129(10), 2315-2327, 2011). Leading the tumor inflammatory response are tumor associated macrophages (TAMs) [R. Noy Immunity, 41(1.49-61, 2014]. A correlation between high numbers of TAMs and rapid disease progression and poor patient outcome has been observed for decades [L. Bingle, Journal of Pathology, 196 (3), 254-265, 2002; B.-Z. Qian Cell, 141(1), 39-51, 2010]; however, only recently was this paradoxical phenotype explained. It is now understand that this correlation is due to TAM-mediated paracrine signaling, in which macrophage derived factors activate the CSC compartment and promote stemlike features of CSCs, exacerbating tumor progression, metastasis, and even CSC chemoresistance.

Monocyte infiltration into a tumor is mediated by chemokines (e.g., CCL2, CCLS, and CXCL12), CSF-1, and components of the complement cascade [E. Bonavita, Advances in Cancer Research, 128, 141-171, 2015; E. Bonavita, Cell, 160(4), 700-714, 2015]. Once they are within the tumor, the tumor environment rapidly promotes their differentiation into tumor-conditioned macrophages. TAMs were initially believed to be biased away from an M1 phenotype, expressing M2 protumor markers [Biswas S K. Nature Immunology, 11(10), 889-896, 2010].

To more specifically identify M2-like TAMs and subsets, the hemoglobin-scavenger receptor CD163 [Heusinkveld M. The Journal of Immunology, 187(3), 1157-1165, 2011; Martinez F O., Annual Review of Immunology, 27, 451-483, 2009], the macrophage scavenger receptor 1 CD204 [Biswas S K. Nature Immunology, 11(10), 889-896, 2010, Laoui, D. International Journal of Developmental Biology, 55(7-9), 861-867, 2011], the mannose receptor CD206 [Mantovani, A. Trends in Immunology, 23(11), 549-555, 2002], the macrophage receptor CD68 (Tang X, Cancer Letter 2013, Takeuchi H, Oncol Lett 2016; Hu H, tumour biol 2016; Kim K J, PlosOne 2015) and more recently the T-cell immunoglobulin andmucin-domain containing protein-3 (Tim-3) [Yan W., Gut, 64(10), 1593-1604, 2015] have been used with great success.

As the important role of tumour microenvironment in promoting cancer initiation and tumour growth is recognized, in particular the role of TAMs, TAMs inhibition and/or depletion represent an attractive anti-cancer immunotherapeutic approach (Noy, R., and Pollard, J. W. 2014. Tumor-associated macrophages: from mechanisms to therapy. Immunity 41:49-61). However, very few drugs are developed and clinical-stage "anti-TAM" therapies include mainly targeting of CD115 (a functional marker of TAMs) (Cassier, P. A., Italiano, A., Gomez-Roca, C. A., Le Tourneau, C., Toulmonde, M., Cannarile, M. A., Ries, C., Brillouet, A., Muller, C., Jegg, A. M., et al. 2015. CSF1R inhibition with emactuzumab in locally advanced diffuse-type tenosynovial giant cell tumours of the soft tissue: a dose-escalation and dose-expansion phase 1 study. Lancet Oncol 16:949-956).

Therefore, there is a need for new drugs targeting TAM present in the tumour. In particular, drugs targeting specific biological markers of TAMs would be highly desirable.

SUMMARY OF THE INVENTION

The present invention relates to antibodies targeting Tumor Associated Macrophages (TAMs) and uses thereof. In particular, the present invention is defined by the claims.

DETAILED DESCRIPTION OF THE INVENTION

The inventors showed the presence of sideroflexin 3 in tumor-associated macrophages (TAMs also called, Nurse like Cells (NLCs) in leukemia), which has never been mentioned in the prior art.

More particularly, inventors present evidence that sideroflexin 3, which is absent in normal macrophage, is expressed by tumors associated macrophage. This is the first specific marker that is exposed on the surface of the macrophage associated tumors, and as a consequence offers unique opportunities for detecting and targeting TAM (for therapy of cancer). The inventors further present evidence that using antibody directed sideroflexin 3, they depleted in PBMC sample obtained from LCC patient, TAMs and strongly reduced leukemic B cells number.

Here the inventors investigated specific marker exposed on the surface of the macrophage associated tumor in order to detect and target TAMs. By immunizing mice with TAMs obtained from LCC patient they recover, between 200 fractions, four antibodies fractions (four hybridomas including one sub-type: 6-16, 6-25, 6-66-49 and 6-66-74) able to recognize specifically TAMs. Surprisingly, sequencing experiments showed that the 3 hybridomas have the same VH & VL sequences. They found surprisingly that 1) antibodies in the fractions were able to recognize the sideroflexin 3 protein specifically expressed at the surface of macrophage associated tumors 2) antibodies were specific to the TAMs and did not recognized other PBMCs from patients or healthy donors (like lymphocytes B and T), or tumour cells 3) use of sideroflexin 3 antibodies in PBMC sample obtained from LCC patient, depleted TAMs and reduced tumor cells number and 4) sideroflexin 3 antibodies were also able to detect TAMs present in breast tumor sample. These results show that targeting sideroflexin 3 expressed on TAMS therefore allows restoring beneficial anti-tumor immunity in cancer.

Antibodies of the Invention

In one embodiment, the antibody of the present invention comprises:

(a) a heavy chain wherein the variable domain comprises:
  a H-CDR1 having 90, 91, 92, 93, 94, 95, 96, 97, 98 or 99% of identity with the sequence set forth as SEQ ID NO: 1, and a H-CDR2 having 90, 91, 92, 93, 94, 95, 96, 97, 98 or 99% of identity with the sequence set forth as SEQ ID NO: 2, and a H-CDR3 having 90, 91, 92, 93, 94, 95, 96, 97, 98 or 99% of identity with the sequence set forth as SEQ ID NO: 3;

(b) a light chain wherein the variable domain comprises:

a L-CDR1 having 90, 91, 92, 93, 94, 95, 96, 97, 98 or 99% of identity with the sequence set forth as SEQ ID NO: 4, and a L-CDR2 having 90, 91, 92, 93, 94, 95, 96, 97, 98 or 99% of identity with the sequence set forth as SEQ ID NO: 5, and a L-CDR3 having 90, 91, 92, 93, 94, 95, 96, 97, 98 or 99% of identity with the sequence set forth as SEQ ID NO: 6.

(c) that binds to sideroflexin-3 with substantially the same affinity as an antibody having a variable light chain domain (VL) and/or a variable heavy chain domain (VH) of the antibody 6-25.

In one embodiment, the antibody of the present invention comprises:

(a) a heavy chain wherein the variable domain comprises:
a H-CDR1 having a sequence set forth as SEQ ID NO: 1, and
a H-CDR2 having a sequence set forth as SEQ ID NO: 2, and
a H-CDR3 having a sequence set forth as SEQ ID NO: 3;
(b) a light chain wherein the variable domain comprises:
a L-CDR1 having a sequence set forth as SEQ ID NO: 4, and
a L-CDR2 having a sequence set forth as SEQ ID NO: 5, and
a L-CDR3 having a sequence set forth as SEQ ID NO: 6.

In one embodiment, the antibody of the present invention comprises:

a heavy chain wherein the variable domain has at least 70% of identity with the sequence set forth as SEQ ID NO:7 a light chain wherein the variable domain has at least 70% of identity with the sequence set forth as SEQ ID NO:8 and binds to sideroflexin-3 with substantially the same affinity as an antibody having a variable light chain domain (VL) and/or a variable heavy chain domain (VH) of the antibody 6-25.

In one embodiment, the antibody of the present invention comprises:

a heavy chain wherein the variable domain has at least 80% of identity with the sequence set forth as SEQ ID NO:7 a light chain wherein the variable domain has at least 80% of identity with the sequence set forth as SEQ ID NO:8 and binds to sideroflexin-3 with substantially the same affinity as an antibody having a variable light chain domain (VL) and/or a variable heavy chain domain (VH) of the antibody 6-25.

In one embodiment, the antibody of the present invention comprises:

a heavy chain wherein the variable domain has 90, 91, 92, 93, 94, 95, 96, 97, 98 or 99% of identity with the sequence set forth as SEQ ID NO:7 a light chain wherein the variable domain has 90, 91, 92, 93, 94, 95, 96, 97, 98 or 99% of identity with the sequence set forth as SEQ ID NO:8 and binds to sideroflexin-3 with substantially the same affinity as an antibody having a variable light chain domain (VL) and/or a variable heavy chain domain (VH) of the antibody 6-25.

In one embodiment, the antibody of the present invention comprises:

a heavy chain wherein the variable domain has a sequence set forth as SEQ ID NO:7 a light chain wherein the variable domain has a sequence set forth as SEQ ID NO:8

In a particular embodiment, the antibody of the present invention is able to deplete Tumor Associated Macrophages.

Tests for assessing the depletion of TAMs are well known in the art. For instance, the following test assesses the depletion of NLC with the anti-CSF-1R: Avery Polk, Ye Lu, Tianjiao Wang, Erlene Seymour, Nathanael G. Bailey, Jack W. Singer, Philip S. Boonstra, Megan S. Lim, Sami Malek, and Ryan A. Wilcox. 2016. Colony-stimulating Factor-1 Receptor is Required for Nurse-like Cell Survival in Chronic Lymphocytic Leukemia. Clin. Cancer Res. June 22. pii: clincanres.3099.2015.

The sequences of interest in the present application are indicated in the following

TABLE 1

| Name | SEQ ID | Sequence |
|---|---|---|
| H-CDR1 | SEQ ID NO: 1 | GFSLTGYG |
| H-CDR2 | SEQ ID NO: 2 | IWGDGST |
| H-CDR3 | SEQ ID NO: 3 | ARDLKFAYW |
| L-CDR1 | SEQ ID NO: 4 | QHVTTA |
| L-CDR2 | SEQ ID NO: 5 | SAS |
| L-CDR3 | SEQ ID NO: 6 | QQHYTTPWT |
| H-VD | SEQ ID NO: 7 | QVQLKESGPGLVAPSQSLSITCTVSGFSLT GYGVNWVRQPPGKGLEWLGMIWGDGSTDYNS DLKSRLSITEDNSKRQVFLKMDSLQTEDTARYYC ARDLKFAYWGQGTLVTVSA |
| L-VD | SEQ ID NO: 8 | DIVMTQSHKFMSSSVGDRVSITCKASQHV TTAVAWFQQKPGQSPKLLIYSASFRYTGVPDRFT GSGSGTDFTFTISTVQAEDLAVYYCQQHYTTPWT EGGGTKLEIK |

TABLE 1-continued

| Name | SEQ ID | Sequence |
|---|---|---|
| H-VD nucleic acid sequence | SEQ ID NO: 9 | CAGGTGCAGCTGAAGGAGTCAGGACCTG GCCTGGTGGCGCCCTCACAGAGCCTGTCCATCA CATGCACCGTCTCAGGGTTCTCATTAACCGGCT ATGGTGTAAACTGGGTTCGCCAGCCTCCAGGAA GGGTCTGGAGTGGCTGGGAATGATATGGGGTG ATGGAAGCACAGACTATAATTCAGATCTCAAAT CCAGACTGAGCATCACCGAGGACAACTCCAAG CGCCAAGTTTTCTTAAAAATGGACAGTCTGAAA CTGAAGACACAGCCAGGTACTACTGTGCCAGA GATCTTAAGTTTGCTTACTGGGGCCAAGGGACT CTGGTCACTGTCTCTGCA |
| L-VD nucleic acid sequence | SEQ ID NO: 10 | GACATTGTGATGACCCAGTCTCACAAATT CATGTCCTCATCAGTAGGAGACAGGGTCAGCAT CACCTGCAAGGCCAGTCAACATGTGACTACTGC TGTTGCCTGGTTTCAACAGAAACCAGGACAATT CCTAAACTACTGATTTACTCGGCATCCTTCCGGT ACACTGGAGTCCCTGATCGCTTCACTGGCAGTG GATCTGGGACGGATTTCACTTTCACCATCAGCA CTGTGCAGGCTGAAGACCTGGCAGTTATTACTG TCAGCAACATTATACTACTCCGTGGACGTTCGG TGGAGGCACCAAGCTGGAAATCAAA |

As used herein the term "antibody" or "immunoglobulin" have the same meaning, and will be used equally in the present invention. The term "antibody" as used herein refers to immunoglobulin molecules and immunologically active portions of immunoglobulin molecules, i.e., molecules that contain an antigen binding site that immunospecifically binds an antigen. As such, the term antibody encompasses not only whole antibody molecules, but also antibody fragments as well as variants (including derivatives) of antibodies and antibody fragments. In natural antibodies, two heavy chains are linked to each other by disulfide bonds and each heavy chain is linked to a light chain by a disulfide bond. There are two types of light chain, lambda (l) and kappa (κ). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, trans-placental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) can participate to the antibody binding site or influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, typically includes six CDRs, comprising the CDR set from each of a heavy and a light chain V region. Framework Regions (FRs) refer to amino acid sequences interposed between CDRs. In the context of the invention, the amino acid residues of the antibody of the invention are numbered according to the IMGT numbering system. The IMGT unique numbering has been defined to compare the variable domains whatever the antigen receptor, the chain type, or the species (Lefranc M.-P., "Unique database numbering system for immunogenetic analysis" Immunology Today, 18, 509 (1997); Lefranc M.-P., "The IMGT unique numbering for Immunoglobulins, T cell receptors and Ig-like domains" The Immunologist, 7, 132-136 (1999); Lefranc, M.-P., Pommié, C., Ruiz, M., Giudicelli, V., Foulquier, E., Truong, L., Thouvenin-Contet, V. and Lefranc, G., "IMGT unique numbering for immunoglobulin and T cell receptor variable domains and Ig superfamily V-like domains" Dev. Comp. Immunol., 27, 55-77 (2003).). In the IMGT unique numbering, the conserved amino acids always have the same position, for instance cysteine 23, tryptophan 41, hydrophobic amino acid 89, cysteine 104, phenylalanine or tryptophan 118. The IMGT unique numbering provides a standardized delimitation of the framework regions (FR1-IMGT: positions 1 to 26, FR2-IMGT: 39 to 55, FR3-IMGT: 66 to 104 and FR4-IMGT: 118 to 128) and of the complementarity determining regions: CDR1-IMGT: 27 to 38, CDR2-IMGT: 56 to 65 and CDR3-IMGT: 105 to 117. If the CDR3-IMGT length is less than 13 amino acids, gaps are created from the top of the loop, in the following order 111, 112, 110, 113, 109, 114, etc. If the CDR3-IMGT length is more than 13 amino acids, additional positions are created between positions 111 and 112 at the top of the CDR3-IMGT loop in the following order 112.1, 111.1, 112.2, 111.2, 112.3, 111.3, etc. (http://www.imgt.org/IMGTScientificChart/Nomenclature/IMGT-FRCDRdefinition.html).

As used herein, the term "specificity" refers to the ability of an antibody to detectably bind an epitope presented on an antigen, such as sideroflexin-3, while having relatively little detectable reactivity with non-sideroflexin-3 proteins or structures (such as other proteins expressed on TAM, or on other cell types). Specificity can be relatively determined by binding or competitive binding assays, using, e.g., Biacore instruments, as described elsewhere herein. Specificity can be exhibited by, e.g., an about 10:1, about 20:1, about 50:1, about 100:1, 10.000:1 or greater ratio of affinity/avidity in binding to the specific antigen versus nonspecific binding to other irrelevant molecules (in this case the specific antigen is sideroflexin-3).

The term "affinity", as used herein, means the strength of the binding of an antibody to an epitope. The affinity of an antibody is given by the dissociation constant Kd, defined as [Ab]×[Ag]/[Ab-Ag], where [Ab-Ag] is the molar concentration of the antibody-antigen complex, [Ab] is the molar concentration of the unbound antibody and [Ag] is the molar concentration of the unbound antigen. The affinity constant Ka is defined by 1/Kd. Preferred methods for determining the affinity of mAbs can be found in Harlow, et al., Antibodies: A Laboratory Manual, Cold Spring Harbor Laboratory Press, Cold Spring Harbor, N.Y., 1988), Coligan et al., eds., Current Protocols in Immunology, Greene Publishing Assoc. and Wiley Interscience, N.Y., (1992, 1993), and Muller, Meth. Enzymol. 92:589-601 (1983), which references are entirely incorporated herein by reference. One preferred and standard method well known in the art for determining the affinity of mAbs is the use of Biacore instruments.

The antibody of the invention may be assayed for specific binding by any method known in the art. Many different competitive binding assay format(s) can be used for epitope binding. The immunoassays which can be used include, but are not limited to, competitive assay systems using techniques such western blots, radioimmunoassays, ELISA, "sandwich" immunoassays, immunoprecipitation assays, precipitin assays, gel diffusion precipitin assays, immunoradiometric assays, fluorescent immunoassays, protein A immunoassays, and complement-fixation assays. Such assays are routine and well known in the art (see, e.g., Ausubel et al., eds, 1994 Current Protocols in Molecular Biology, Vol. 1, John Wiley & sons, Inc., New York). For example, the BIACORE® (GE Healthcare, Piscaataway, N.J.) is one of a variety of surface plasmon resonance assay formats that are routinely used to epitope bin panels of monoclonal antibodies. Additionally, routine cross-blocking assays such as those described in Antibodies, A Laboratory Manual, Cold Spring Harbor Laboratory, Ed Harlow and David Lane, 1988, can be performed.

The terms "monoclonal antibody", "monoclonal Ab", "monoclonal antibody composition", "mAb", or the like, as used herein refer to a preparation of antibody molecules of single molecular composition. A monoclonal antibody composition displays a single binding specificity and affinity for a particular epitope.

As used herein, the percent identity between two sequences is a function of the number of identical positions shared by the sequences (i. e., % identity=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described below.

The percent identity between two amino acid sequences can be determined using the algorithm of E. Myers and W. Miller (Comput. Appl. Biosci. 4: 1 1-17, 1988) which has been incorporated into the ALIGN program. In addition, the percent identity between two amino acid sequences can be determined using the Needleman and Wunsch (J. Mol. Biol. 48:443-453, 1970) algorithm which has been incorporated into the GAP program in the GCG software package. Yet another program to determine percent identity is CLUSTAL (M. Larkin et al., Bioinformatics 23:2947-2948, 2007; first described by D. Higgins and P. Sharp, Gene 73:237-244, 1988) which is available as stand-alone program or via web servers (see http://www.clustal.org/).

The percent identity between two nucleotide amino acid sequences may also be determined using for example algorithms such as the BLASTN program for nucleic acid sequences using as defaults a word length (W) of 11, an expectation (E) of 10, M=5, N=4, and a comparison of both strands.

As used herein, the term "sideroflexin 3" or "SFXN3", also known as "SFX3;", or "BA108L7.2" is a one member of Sideroflexin proteins and refers to a protein that in humans is encoded by the SFXN3 gene [Gene ID: 81855]. Sideroflexin is commonly referred to as proteins involved in iron transport in mitochondria. In addition, the human Sideroflexin is also reported to play an important role in the differentiation of pancreatic β cells (Yoshikumi Y, J Cell Biochem., 95, 1157-1168 (2005)). One example of wild-type sideroflexin 3 human amino acid sequence is provided on NCBI website, reference sequence: NP_112233. One example of nucleotide sequence encoding wild-type sideroflexin 3 amino acid sequence is provided on NCBI website, reference sequence: NM_030971.

The term "tumor associated macrophage" or "TAM" has its general meaning in the art and is intended to describe a type of cell belonging to the macrophage lineage. They are found in close proximity or within tumor masses [Shih, J-Y., Journal of Cancer Molecules 2(3): 101-106 2006]. TAMs are derived from circulating monocytes or resident tissue macrophages, which form the major leukocytic infiltrate found within the stroma of many tumor types. There is growing evidence for their involvement in pro-tumor (e.g. promotion of growth and metastasis through tumor angiogenesis) processes [Birbrair, A. American Journal of Physiology. Cell Physiology 307 (1): C25-C38. 2014; Thoreau, M; Oncotarget 6(29) 27832-27832 2015]. TAMs interact with a wide range of growth factors, cytokines and chemokines in the tumor microenvironment which is thought to educate the TAMs and determine their specific phenotype and hence functional role as the microenvironment varies between different types of tumors. TAMs have therefore been shown to differ in their roles depending on the type of tumor with which they are associated [Lewis, C E; Cancer Research 66 (2): 605-612. (2006)]. In many tumor types TAM infiltration level has been shown to be of significant prognostic value. TAMs have been linked to poor prognosis in breast cancer, ovarian cancer, types of glioma and lymphoma; better prognosis in colon and stomach cancers and both poor and better prognoses in lung and prostate cancers [Allavena, P. Critical Reviews in Oncology/Hematology 66: 1. (2008)]. In leukemia TAMs are also called Nurse like Cells (NLCs).

The demonstration of regulatory/suppressive function of TAM cells may be determined by any suitable method known in the art (Qian B Z and Pollard J W, Cell, 2010, vol 141, 1:39-41). In particular, examples of such tests are set out in the example section. Specifically, the tests embodied in example are regarded as standards in vitro tests for the assessment of TAM function.

In some embodiments, Tumor associated macrophage according to the present invention are mammalian Tumor associated macrophage, most particularly human Tumor associated macrophage.

In one embodiment, the antibody of the present invention is defined according to the Kabat system.

The residues in antibody variable domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al."). The Kabat residue designations do not always correspond directly with the linear numbering of the amino acid residues in SEQ ID sequences. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence. The CDRs of the heavy chain variable domain are located at residues 31-35B (H-CDR1), residues 50-65 (H-CDR2) and residues 95-102 (H-CDR3) according to the Kabat numbering system. The CDRs of the light chain variable domain are located at residues 24-34 (L-CDR1), residues 50-56 (L-CDR2) and residues 89-97 (L-CDR3) according to the Kabat numbering system.

According to the Kabat system, the six CDRs of the antibody of the invention are:

H-CDR1: SEQ ID NO:11: GFSLTGY;
H-CDR2: SEQ ID NO:12: WGDGS;
H-CDR3: SEQ ID NO:13: DLKFAY;
L-CDR1: SEQ ID NO:14: KASQHVTTAVA;
L-CDR2: SEQ ID NO:15: SASFRYT;
L-CDR3: SEQ ID NO:16: QQHYTTPWT.

In one embodiment, the antibody of the invention comprises:

(a) a heavy chain wherein the variable domain comprises:
a H-CDR1 having 90, 91, 92, 93, 94, 95, 96, 97, 98 or 99% of identity with the sequence set forth as SEQ ID NO:11;
a H-CDR2 having 90, 91, 92, 93, 94, 95, 96, 97, 98 or 99% of identity with the sequence set forth as SEQ ID NO:12;
a H-CDR3 having 90, 91, 92, 93, 94, 95, 96, 97, 98 or 99% of identity with the sequence set forth as SEQ ID NO:13;
(b) a light chain wherein the variable domain comprises:
a L-CDR1 having 90, 91, 92, 93, 94, 95, 96, 97, 98 or 99% of identity with the sequence set forth as SEQ ID NO:14;
a L-CDR2 having 90, 91, 92, 93, 94, 95, 96, 97, 98 or 99% of identity with the sequence set forth as SEQ ID NO:15;
a L-CDR3 having 90, 91, 92, 93, 94, 95, 96, 97, 98 or 99% of identity with the sequence set forth as SEQ ID NO:16.
(c) that binds to sideroflexin-3 with substantially the same affinity as an antibody having a variable light chain domain (VL) and/or a variable heavy chain domain (VH) of the antibody 6-25.

In one embodiment, the antibody of the invention comprises:

(a) a heavy chain wherein the variable domain comprises:
a H-CDR1 having a sequence set forth as SEQ ID NO:11;
a H-CDR2 having a sequence set forth as SEQ ID NO:12;
a H-CDR3 having a sequence set forth as SEQ ID NO:13;
(b) a light chain wherein the variable domain comprises:
a L-CDR1 having a sequence set forth as SEQ ID NO:14;
a L-CDR2 having a sequence set forth as SEQ ID NO:15;
a L-CDR3 having a sequence set forth as SEQ ID NO:16.

The antibodies of the present invention are produced by any technique known in the art, such as, without limitation, any chemical, biological, genetic or enzymatic technique, either alone or in combination. Typically, knowing the amino acid sequence of the desired sequence, one skilled in the art can readily produce said antibodies, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions. Alternatively, antibodies of the present invention can be synthesized by recombinant DNA techniques well-known in the art. For example, antibodies can be obtained as DNA expression products after incorporation of DNA sequences encoding the antibodies into expression vectors and introduction of such vectors into suitable eukaryotic or prokaryotic hosts that will express the desired antibodies, from which they can be later isolated using well-known techniques.

In one embodiment, the monoclonal antibody of the invention is a chimeric antibody, particularly a chimeric mouse/human antibody.

According to the invention, the term "chimeric antibody" refers to an antibody which comprises a VH domain and a VL domain of a non-human antibody, and a CH domain and a CL domain of a human antibody.

In some embodiments, the human chimeric antibody of the present invention can be produced by obtaining nucleic sequences encoding VL and VH domains as previously described, constructing a human chimeric antibody expression vector by inserting them into an expression vector for animal cell having genes encoding human antibody CH and human antibody CL, and expressing the coding sequence by introducing the expression vector into an animal cell. As the CH domain of a human chimeric antibody, it may be any region which belongs to human immunoglobulin, but those of IgG class are suitable and any one of subclasses belonging to IgG class, such as IgG1, IgG2, IgG3 and IgG4, can also be used. Also, as the CL of a human chimeric antibody, it may be any region which belongs to Ig, and those of kappa class or lambda class can be used. Methods for producing chimeric antibodies involve conventional recombinant DNA and gene transfection techniques are well known in the art (See Morrison S L. et al. (1984) and patent documents U.S. Pat. Nos. 5,202,238; and 5,204,244).

In another embodiment, the monoclonal antibody of the invention is a humanized antibody. In particular, in said humanized antibody, the variable domain comprises human acceptor frameworks regions, and optionally human constant domain where present, and non-human donor CDRs, such as mouse CDRs.

In another embodiment, the monoclonal antibody of the invention is a caninized or primatized based on the same methods of humanization.

According to the invention, the term "humanized antibody" refers to an antibody having variable region framework and constant regions from a human antibody but retains the CDRs of a previous non-human antibody.

The humanized antibody of the present invention may be produced by obtaining nucleic acid sequences encoding CDR domains, as previously described, constructing a humanized antibody expression vector by inserting them into an expression vector for animal cell having genes encoding (i) a heavy chain constant region identical to that of a human antibody and (ii) a light chain constant region identical to that of a human antibody, and expressing the genes by introducing the expression vector into an animal cell. The humanized antibody expression vector may be either of a type in which a gene encoding an antibody heavy chain and a gene encoding an antibody light chain exists on separate vectors or of a type in which both genes exist on the same vector (tandem type). In respect of easiness of construction of a humanized antibody expression vector, easiness of introduction into animal cells, and balance between the expression levels of antibody H and L chains in animal cells, humanized antibody expression vector of the tandem type is preferred. Examples of tandem type humanized antibody expression vector include pKANTEX93 (WO 97/10354), pEE18 and the like. Methods for producing humanized antibodies based on conventional recombinant DNA and gene transfection techniques are well known in the art (See, e. g., Riechmann L. et al. 1988; Neuberger M S. et al. 1985). Antibodies can be humanized using a variety of techniques known in the art including, for example, CDR-grafting (EP 239,400; PCT publication WO91/09967; U.S. Pat. Nos. 5,225,539; 5,530,101; and 5,585,089), veneering or resurfacing (EP 592,106; EP 519,596; Padlan E A (1991); Studnicka G M et al. (1994); Roguska M A. et al. (1994)), and chain shuffling (U.S. Pat. No. 5,565,332). The general recombinant DNA technology for preparation of such antibodies is also known (see European Patent Application EP 125023 and International Patent Application WO 96/02576).

Fragments of the Antibody of the Present Invention

In one embodiment, the antibody of the invention is an antigen binding fragment selected from the group consisting of a Fab, a F(ab)'2, a single domain antibody, a ScFv, a Sc(Fv)2, a diabody, a triabody, a tetrabody, an unibody, a minibody, a maxibody, a small modular immunopharmaceutical (SMIP), minimal recognition units consisting of the amino acid residues that mimic the hypervariable region of an antibody as an isolated complementary determining region (CDR), and fragments which comprise or consist of the VL or VH chains as well as amino acid sequence having at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100% of identity with SEQ ID NO:7 or SEQ ID NO:8.

The term "antigen binding fragment" of an antibody, as used herein, refers to one or more fragments of an intact antibody that retain the ability to specifically binds to a given antigen (e.g., sideroflexin-3). Antigen biding functions of an antibody can be performed by fragments of an intact antibody. Examples of biding fragments encompassed within the term antigen biding fragment of an antibody include a Fab fragment, a monovalent fragment consisting of the VL, VH, CL and CH1 domains; a Fab' fragment, a monovalent fragment consisting of the VL, VH, CL, CH1 domains and hinge region; a F(ab')2 fragment, a bivalent fragment comprising two Fab' fragments linked by a disulfide bridge at the hinge region; an Fd fragment consisting of VH domains of a single arm of an antibody; a single domain antibody (sdAb) fragment (Ward et al., 1989 Nature 341:544-546), which consists of a VH domain or a VL domain; and an isolated complementary determining region (CDR). Furthermore, although the two domains of the Fv fragment, VL and VH, are coded for by separate genes, they can be joined, using recombinant methods, by an artificial peptide linker that enables them to be made as a single protein chain in which the VL and VH regions pair to form monovalent molecules (known as single chain Fv (ScFv); see, e.g., Bird et al., 1989 Science 242:423-426; and Huston et al., 1988 proc. Natl. Acad. Sci. 85:5879-5883). "dsFv" is a VH::VL heterodimer stabilized by a disulfide bond. Divalent and multivalent antibody fragments can form either spontaneously by association of monovalent scFvs, or can be generated by coupling monovalent scFvs by a peptide linker, such as divalent sc(Fv)2. Such single chain antibodies include one or more antigen biding portions or fragments of an antibody. These antibody fragments are obtained using conventional techniques known to those skilled in the art, and the fragments are screened for utility in the same manner as are intact antibodies. A unibody is another type of antibody fragment lacking the hinge region of IgG4 antibodies. The deletion of the hinge region results in a molecule that is essentially half the size of traditional IgG4 antibodies and has a univalent binding region rather than the bivalent biding region of IgG4 antibodies. Antigen binding fragments can be incorporated into single domain antibodies, SMIP, maxibodies, minibodies, intrabodies, diabodies, triabodies and tetrabodies (see, e.g., Hollinger and Hudson, 2005, Nature Biotechnology, 23, 9, 1126-1136). The term "diabodies" "triabodies" or "tetrabodies" refers to small antibody fragments with multivalent antigen-binding sites (2, 3 or four), which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Antigen biding fragments can be incorporated into single chain molecules comprising a pair of tandem Fv segments (VH-CH1-VH-CH1) Which, together with complementary light chain polypeptides, form a pair of antigen binding regions (Zapata et al., 1995 Protein Eng. 8(10); 1057-1062 and U.S. Pat. No. 5,641,870).

The Fab of the present invention can be obtained by treating an antibody which specifically reacts with sideroflexin-3 with a protease, papaine. Also, the Fab can be produced by inserting DNA encoding Fab of the antibody into a vector for prokaryotic expression system, or for eukaryotic expression system, and introducing the vector into a procaryote or eucaryote (as appropriate) to express the Fab.

The F(ab')2 of the present invention can be obtained treating an antibody which specifically reacts with sideroflexin-3 with a protease, pepsin. Also, the F(ab')2 can be produced by binding Fab' described below via a thioether bond or a disulfide bond.

The Fab' of the present invention can be obtained treating F(ab')2 which specifically reacts with sideroflexin-3 with a reducing agent, dithiothreitol. Also, the Fab' can be produced by inserting DNA encoding Fab' fragment of the antibody into an expression vector for prokaryote, or an expression vector for eukaryote, and introducing the vector into a prokaryote or eukaryote (as appropriate) to perform its expression.

The scFv of the present invention can be produced by obtaining cDNA encoding the VH and VL domains as previously described, constructing DNA encoding scFv, inserting the DNA into an expression vector for prokaryote, or an expression vector for eukaryote, and then introducing the expression vector into a prokaryote or eukaryote (as appropriate) to express the scFv. To generate a humanized scFv fragment, a well-known technology called CDR grafting may be used, which involves selecting the complementary determining regions (CDRs) from a donor scFv fragment, and grafting them onto a human scFv fragment framework of known three dimensional structure (see, e. g., WO98/45322; WO 87/02671; U.S. Pat. Nos. 5,859,205; 5,585,089; 4,816,567; EP0173494).

Domain Antibodies (dAbs) are the smallest functional binding units of antibodies—molecular weight approximately 13 kDa—and correspond to the variable regions of either the heavy (VH) or light (VL) chains of antibodies. Further details on domain antibodies and methods of their production are found in U.S. Pat. Nos. 6,291,158; 6,582,915; 6,593,081; 6,172,197; and 6,696,245; US 2004/0110941; EP 1433846, 0368684 and 0616640; WO 2005/035572, 2004/101790, 2004/081026, 2004/058821, 2004/003019 and 2003/002609, each of which is herein incorporated by reference in its entirety.

UniBodies are another antibody fragment technology, based upon the removal of the hinge region of IgG4 antibodies. The deletion of the hinge region results in a molecule that is essentially half the size of a traditional IgG4 antibody and has a univalent binding region rather than a bivalent binding region. Furthermore, because UniBodies are about smaller, they may show better distribution over larger solid tumors with potentially advantageous efficacy. Further details on UniBodies may be obtained by reference to WO 2007/059782, which is incorporated by reference in its entirety.

Nucleic Acid Molecule, Vector, Host Cells

A further object of the invention relates to a nucleic acid molecule encoding an antibody according to the invention. More particularly the nucleic acid molecule encodes a heavy chain or a light chain of an antibody of the present invention.

In a particular embodiment, the nucleic acid molecule comprises a nucleic acid sequence having at least 70% of identity with SEQ ID NO:9 or SEQ ID NO:10.

More particularly the nucleic acid molecule comprises a nucleic acid sequence having at least 80% of identity with SEQ ID NO:9 or SEQ ID NO:10.

More particularly the nucleic acid molecule comprises a nucleic acid sequence having at least 90% of identity with SEQ ID NO:9 or SEQ ID NO:10.

More particularly the nucleic acid molecule comprises a nucleic acid sequence having at least 91, 92, 93, 94, 95, 96, 97, 98 or 99% of identity with SEQ ID NO:9 or SEQ ID NO:10.

Variable domain Heavy chain: nucleic acid sequence FR1-CDR1-FR2-CDR2-FR3-CDR3-FR4: SEQ ID NO:9

```
CAGGTGCAGCTGAAGGAGTCAGGACCTGGCCTGGTGGCGCCCTCACA

GAGCCTGTCCATCACATGCACCGTCTCAGGGTTCTCATTAACCGGCTATGG

TGTAAACTGGGTTCGCCAGCCTCCAGGAAGGGTCTGGAGTGGCTGGGAATG

ATATGGGGTGATGGAAGCACAGACTATAATTCAGATCTCAAATCCAGACTG

AGCATCACCGAGGACAACTCCAAGCGCCAAGTTTTCTTAAAAATGGACAGT

CTGAAACTGAAGACACAGCCAGGTACTACTGTGCCAGAGATCTTAAGTTTG

CTTACTGGGGCCAAGGGACTCTGGTCACTGTCTCTGCA
```

Variable domain Light chain: nucleic acid sequence FR1-CDR1-FR2-CDR2-FR3-CDR3-FR4: SEQ ID NO:10

```
GACATTGTGATGACCCAGTCTCACAAATTCATGTCCTCATCAGTAGG

AGACAGGGTCAGCATCACCTGCAAGGCCAGTCAACATGTGACTACTGCTGT

TGCCTGGTTTCAACAGAAACCAGGACAATTCCTAAACTACTGATTTACTCG

GCATCCTTCCGGTACACTGGAGTCCCTGATCGCTTCACTGGCAGTGGATCT

GGGACGGATTTCACTTTCACCATCAGCACTGTGCAGGCTGAAGACCTGGCA

GTTATTACTGTCAGCAACATTATACTACTCCGTGGACGTTCGGTGGAGGCA

CCAAGCTGGAAATCAAA
```

Typically, said nucleic acid is a DNA or RNA molecule, which may be included in any suitable vector, such as a plasmid, cosmid, episome, artificial chromosome, phage or a viral vector. As used herein, the terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence. So, a further aspect of the invention relates to a vector comprising a nucleic acid of the invention. Such vectors may comprise regulatory elements, such as a promoter, enhancer, terminator and the like, to cause or direct expression of said antibody upon administration to a subject. Examples of promoters and enhancers used in the expression vector for animal cell include early promoter and enhancer of SV40 (Mizukami T. et al. 1987), LTR promoter and enhancer of Moloney mouse leukemia virus (Kuwana Y et al. 1987), promoter (Mason J O et al. 1985) and enhancer (Gillies S D et al. 1983) of immunoglobulin H chain and the like. Examples of suitable vectors include pAGE107 (Miyaji H et al. 1990), pAGE103 (Mizukami T et al. 1987), pHSG274 (Brady G et al. 1984), pKCR (O'Hare K et al. 1981), pSG1 beta d2-4-(Miyaji H et al. 1990) and the like. Other examples of plasmids include replicating plasmids comprising an origin of replication, or integrative plasmids, such as for instance pUC, pcDNA, pBR, and the like. Other examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. Nos. 5,882,877, 6,013,516, 4,861,719, 5,278,056 and WO 94/19478.

A further aspect of the invention relates to a host cell which has been transfected, infected or transformed by a nucleic acid and/or a vector according to the invention.

The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA bas been "transformed".

The nucleic acids of the invention may be used to produce an antibody of the present invention in a suitable expression system. The term "expression system" means a host cell and compatible vector under suitable conditions, e.g. for the expression of a protein coded for by foreign DNA carried by the vector and introduced to the host cell. Common expression systems include E. coli host cells and plasmid vectors, insect host cells and Baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include E. coli,

*Kluyveromyces* or *Saccharomyces* yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). Examples also include mouse SP2/0-Ag14 cell (ATCC CRL1581), mouse P3X63-Ag8.653 cell (ATCC CRL1580), CHO cell in which a dihydrofolate reductase gene (hereinafter referred to as "DHFR gene") is defective (Urlaub G et al; 1980), rat YB2/3HL.P2.G11.16Ag.20 cell (ATCC CRL1662, hereinafter referred to as "YB2/0 cell"), and the like. The present invention also relates to a method of producing a recombinant host cell expressing an antibody according to the invention, said method comprising the steps of: (i) introducing in vitro or ex vivo a recombinant nucleic acid or a vector as described above into a competent host cell, (ii) culturing in vitro or ex vivo the recombinant host cell obtained and (iii), optionally, selecting the cells which express and/or secrete said antibody. Such recombinant host cells can be used for the production of antibodies of the present invention. Antibodies of the present invention are suitably separated from the culture medium by conventional immunoglobulin purification procedures such as, for example, protein A-Sepharose, hydroxylapatite chromatography, gel electrophoresis, dialysis, or affinity chromatography.

Functional Variants and Competitive Antibodies

The present invention provides antibodies comprising functional variants of the VL region, VH region, or one or more CDRs of the 6-25 antibody. A functional variant of a VL, VH, or CDR used in the context of a monoclonal antibody of the present invention still allows the antibody to retain at least a substantial proportion (at least about 50%, 60%, 70%, 80%, 90%, 95% or more) of the affinity/avidity and/or the specificity/selectivity of the parent antibody (i.e. 6-25 antibody) and in some cases such a monoclonal antibody of the present invention may be associated with greater affinity, selectivity and/or specificity than the parent Ab. Such variants can be obtained by a number of affinity maturation protocols including mutating the CDRs (Yang et al., J. Mol. Biol., 254, 392-403, 1995), chain shuffling (Marks et al., Bio/Technology, 10, 779-783, 1992), use of mutator strains of *E. coli* (Low et al., J. Mol. Biol., 250, 359-368, 1996), DNA shuffling (Patten et al., Curr. Opin. Biotechnol., 8, 724-733, 1997), phage display (Thompson et al., J. Mol. Biol., 256, 77-88, 1996) and sexual PCR (Crameri et al., Nature, 391, 288-291, 1998). Vaughan et al. (supra) discusses these methods of affinity maturation. Such functional variants typically retain significant sequence identity to the parent Ab. The sequence of CDR variants may differ from the sequence of the CDR of the parent antibody sequences through mostly conservative substitutions; for instance at least about 35%, about 50% or more, about 60% or more, about 70% or more, about 75% or more, about 80% or more, about 85% or more, about 90% or more, (e.g., about 65-95%, such as about 92%, 93% or 94%) of the substitutions in the variant are conservative amino acid residue replacements. The sequences of CDR variants may differ from the sequence of the CDRs of the parent antibody sequences through mostly conservative substitutions; for instance at least 10, such as at least 9, 8, 7, 6, 5, 4, 3, 2 or 1 of the substitutions in the variant are conservative amino acid residue replacements. In the context of the present invention, conservative substitutions may be defined by substitutions within the classes of amino acids reflected as follows:

Aliphatic residues I, L, V, and M
Cycloalkenyl-associated residues F, H, W, and Y
Hydrophobic residues A, C, F, G, H, I, L, M, R, T, V, W, and Y
Negatively charged residues D and E
Polar residues C, D, E, H, K, N, Q, R, S, and T
Positively charged residues H, K, and R
Small residues A, C, D, G, N, P, S, T, and V
Very small residues A, G, and S
Residues involved in turn A, C, D, E, G, H, K, N, Q, R, S, P, and formation T
Flexible residues Q, T, K, S, G, P, D, E, and R More conservative substitutions groupings include: valine-leucine-isoleucine, phenylalanine-tyrosine, lysine-arginine, alanine-valine, and asparagine-glutamine. Conservation in terms of hydropathic/hydrophilic properties and residue weight/size also is substantially retained in a variant CDR as compared to a CDR of the 6-25 antibody. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophane (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The retention of similar residues may also or alternatively be measured by a similarity score, as determined by use of a BLAST program (e.g., BLAST 2.2.8 available through the NCBI using standard settings BLOSUM62, Open Gap=11 and Extended Gap=1). Suitable variants typically exhibit at least about 70% of identity to the parent peptide. According to the present invention a first amino acid sequence having at least 70% of identity with a second amino acid sequence means that the first sequence has 70; 71; 72; 73; 74; 75; 76; 77; 78; 79; 80; 81; 82; 83; 84; 85; 86; 87; 88; 89; 90; 91; 92; 93; 94; 95; 96; 97; 98; 99; or 100% of identity with the second amino acid sequence. According to the present invention a first amino acid sequence having at least 90% of identity with a second amino acid sequence means that the first sequence has 90; 91; 92; 93; 94; 95; 96; 97; 98; 99; or 100% of identity with the second amino acid sequence.

In some embodiments, the antibody of the present invention is an antibody having a heavy chain comprising i) a H-CDR1 having at least 90; 91; 92; 93; 94; 95; 96; 97; 98; or 99% of identity with the H-CDR1 of the antibody of the invention, ii) a H-CDR2 having at least 90; 91; 92; 93; 94; 95; 96; 97; 98; or 99% of identity with the H-CDR2 of the antibody of the invention and iii) a H-CDR3 having at least 90; 91; 92; 93; 94; 95; 96; 97; 98; or 99% of identity with the H-CDR3 of the antibody of the invention.

In some embodiments, the antibody of the present invention is an antibody having a light chain comprising i) a L-CDR1 having at least 90; 91; 92; 93; 94; 95; 96; 97; 98; or 99% of identity with the L-CDR1 of the antibody of the invention, ii) a L-CDR2 having at least 90; 91; 92; 93; 94; 95; 96; 97; 98; or 99% of identity with the L-CDR2 of the antibody of the invention and iii) a L-CDR3 having at least 90; 91; 92; 93; 94; 95; 96; 97; 98; or 99% of identity with the L-CDR3 of the antibody of the invention.

In some embodiments, the antibody of the present invention is an antibody having a heavy chain comprising i) a H-CDR1 having at least 90; 91; 92; 93; 94; 95; 96; 97; 98; or 99% of identity with the H-CDR1 of the antibody of the invention, ii) a H-CDR2 having at least 90; 91; 92; 93; 94; 95; 96; 97; 98; or 99% of identity with the H-CDR2 of the antibody of the invention and iii) a H-CDR3 having at least 90; 91; 92; 93; 94; 95; 96; 97; 98; or 99% of identity with the H-CDR3 of the antibody of the invention and a light chain comprising i) a L-CDR1 having at least 90; 91; 92; 93; 94; 95; 96; 97; 98; or 99% of identity with the L-CDR1 of the antibody of the invention, ii) a L-CDR2 having at least 90; 91; 92; 93; 94; 95; 96; 97; 98; or 99% of identity with the L-CDR2 of the antibody of the invention and iii) a L-CDR3 having at least 90; 91; 92; 93; 94; 95; 96; 97; 98; or 99% of identity with the L-CDR3 of the antibody of the invention.

In some embodiments, the antibody of the present invention is an antibody having a heavy chain comprising i) the H-CDR1 of the antibody of the invention, ii) the H-CDR2 of the antibody of the invention and iii) the H-CDR3 of the antibody of the invention.

In some embodiments, the antibody of the present invention is an antibody having a light chain comprising i) the L-CDR1 of the antibody of the invention, ii) the L-CDR2 of the antibody of the invention and iii) the L-CDR3 of the antibody of the invention.

In some embodiments, the antibody of the present invention is an antibody having a heavy chain comprising i) the H-CDR1 of the antibody of the invention, ii) the H-CDR2 of the antibody of the invention and iii) the H-CDR3 of the antibody of the invention and a light chain comprising i) the L-CDR1 of the antibody of the invention, ii) the L-CDR2 of the antibody of the invention and iii) the L-CDR3 of the antibody of the invention.

In some embodiments, the antibody of the present invention is an antibody having a heavy chain having at least 70; 71; 72; 73; 74; 75; 76; 77; 78; 79; 80; 81; 82; 83; 84; 85; 86; 87; 88; 89; 90; 91; 92; 93; 94; 95; 96; 97; 98; or 99% of identity with SEQ ID NO:7.

In some embodiments, the antibody of the present invention is an antibody having a light chain having at least 70; 71; 72; 73; 74; 75; 76; 77; 78; 79; 80; 81; 82; 83; 84; 85; 86; 87; 88; 89; 90; 91; 92; 93; 94; 95; 96; 97; 98; or 99% of identity with SEQ ID NO:8.

In some embodiments, the antibody of the present invention is an antibody having a heavy chain having at least 70; 71; 72; 73; 74; 75; 76; 77; 78; 79; 80; 81; 82; 83; 84; 85; 86; 87; 88; 89; 90; 91; 92; 93; 94; 95; 96; 97; 98; or 99% of identity with SEQ ID NO:7 and a light chain having at least 70; 71; 72; 73; 74; 75; 76; 77; 78; 79; 80; 81; 82; 83; 84; 85; 86; 87; 88; 89; 90; 91; 92; 93; 94; 95; 96; 97; 98; or 99% of identity with SEQ ID NO:8.

In some embodiments, the antibody of the present invention is an antibody having a heavy chain which is identical to SEQ ID NO:7.

In some embodiments, the antibody of the present invention is an antibody having a light chain identical to SEQ ID NO:8.

In some embodiments, the antibody of the present invention is an antibody having a heavy chain identical to SEQ ID NO:7 and a light chain identical to SEQ ID NO:8.

In another aspect, the invention provides an antibody that competes for binding to sideroflexin-3 with the antibody of the invention.

As used herein, the term "binding" in the context of the binding of an antibody to a predetermined antigen or epitope typically is a binding with an affinity corresponding to a KD of about $10^{-7}$ M or less, such as about $10^{-8}$ M or less, such as about $10^{-9}$ M or less, about $10^{-10}$ M or less, or about $10^{-11}$ M or even less when determined by for instance surface plasmon resonance (SPR) technology in a BIAcore 3000 instrument using a soluble form of the antigen as the ligand and the antibody as the analyte. BIACORE® (GE Healthcare, Piscaataway, N.J.) is one of a variety of surface plasmon resonance assay formats that are routinely used to epitope bin panels of monoclonal antibodies. Typically, an antibody binds to the predetermined antigen with an affinity corresponding to a KD that is at least ten-fold lower, such as at least 100-fold lower, for instance at least 1,000-fold lower, such as at least 10,000-fold lower, for instance at least 100,000-fold lower than its KD for binding to a non-specific antigen (e.g., BSA, casein), which is not identical or closely related to the predetermined antigen. When the KD of the antibody is very low (that is, the antibody has a high affinity), then the KD with which it binds the antigen is typically at least 10,000-fold lower than its KD for a non-specific antigen. An antibody is said to essentially not bind an antigen or epitope if such binding is either not detectable (using, for example, plasmon resonance (SPR) technology in a BIAcore 3000 instrument using a soluble form of the antigen as the ligand and the antibody as the analyte), or is 100 fold, 500 fold, 1000 fold or more than 1000 fold less than the binding detected by that antibody and an antigen or epitope having a different chemical structure or amino acid sequence.

Antibody Engineering

Engineered antibodies of the invention include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis. Such "backmutated" antibodies are also intended to be encompassed by the invention. Another type of framework modification involves mutating one or more residues within the framework region, or even within one or more CDR regions, to remove T cell-epitopes to thereby reduce the potential immunogenicity of the antibody. This approach is also referred to as "deimmunization" and is described in further detail in U.S. Patent Publication No. 20030153043 by Can et al.

In some embodiments, the glycosylation of an antibody is modified. Glycosylation can be altered to, for example, increase the affinity of the antibody for the antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

In some embodiments, some mutations are made to the amino acids localized in aggregation "hotspots" within and near the first CDR (CDR1) to decrease the antibodies susceptibility to aggregation (see Joseph M. Perchiacca et al., Proteins 2011; 79:2637-2647).

The antibody of the present invention may be of any isotype. The choice of isotype typically will be guided by the desired effector functions. IgG1 and IgG3 are isotypes that mediate such effectors functions as ADCC or CDC, when IgG2 and IgG4 don't or in a lower manner. Either of the light chain constant regions, kappa or lambda, may be used. If desired, the class of a monoclonal antibody of the present invention may be switched by known methods. Typical, class switching techniques may be used to convert one IgG subclass to another, for instance from IgG1 to IgG2. Thus, the effector function of the monoclonal antibodies of the present invention may be changed by isotype switching to, e.g., an IgG1, IgG2, IgG3, IgG4, IgD, IgA, IgE, or IgM antibody for various therapeutic uses.

In some embodiments, the antibody of the present invention is a full-length antibody. In some embodiments, the full-length antibody is an IgG1 antibody. In some embodiments, the full-length antibody is an IgG3 antibody.

In some embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In some embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the complement. This approach is described in further detail in U.S. Pat. Nos. 5,624,821 and 5,648,260, both by Winter et al.

In some embodiments, one or more amino acids selected from amino acid residues can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In some embodiments, the Fc region is modified to increase the ability of the antibody to mediate antibody dependent cellular cytotoxicity (ADCC) and/or to increase the affinity of the antibody for an Fc receptor by modifying one or more amino acids. This approach is described further in PCT Publication WO 00/42072 by Presta. Moreover, the binding sites on IgGI for FcγRI, FcγRII, FcγRIII and FcRn have been mapped and variants with improved binding have been described (see Shields, R. L. et al., 2001 J. Biol. Chem. 276:6591-6604, WO2010106180).

The term "antibody-dependent cell-mediated cytotoxicity" or "ADCC" is a term well understood in the art, and refers to a cell-mediated reaction in which non-specific cytotoxic cells that express Fc receptors (FcRs) recognize bound antibody on a target cell and subsequently cause lysis of the target cell. Non-specific cytotoxic cells that mediate ADCC include natural killer (NK) cells, macrophages, monocytes, neutrophils, and eosinophils.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

Additionally or alternatively, an antibody can be made that has an altered type of glycosylation, such as a hypofucosylated or non-fucosylated antibody having reduced amounts of or no fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the present invention to thereby produce an antibody with altered glycosylation. For example, EP1,176,195 by Hang et al. describes a cell line with a functionally disrupted FUT8 gene, which encodes a fucosyl transferase, such that antibodies expressed in such a cell line exhibit hypofucosylation or are devoid of fucosyl residues. Therefore, in some embodiments, the monoclonal antibodies of the present invention may be produced by recombinant expression in a cell line which exhibit hypofucosylation or non-fucosylation pattern, for example, a mammalian cell line with deficient expression of the FUT8 gene encoding fucosyltransferase. PCT Publication WO 03/035835 by Presta describes a variant CHO cell line, Lec13 cells, with reduced ability to attach fucose to Asn (297)-linked carbohydrates, also resulting in hypofucosylation of antibodies expressed in that host cell (see also Shields, R. L. et al, 2002 J. Biol. Chem. 277:26733-26740). PCT Publication WO 99/54342 by Umana et al. describes cell lines engineered to express glycoprotein-modifying glycosyl transferases (e.g., beta(1,4)-N acetylglucosaminyl-transferase III (GnTIII)) such that antibodies expressed in the engineered cell lines exhibit increased bisecting GlcNac structures which results in increased ADCC activity of the antibodies (see also Umana et al, 1999 Nat. Biotech. 17: 176-180). Eureka Therapeutics further describes genetically engineered CHO mammalian cells capable of producing antibodies with altered mammalian glycosylation pattern devoid of fucosyl residues (http://www.eurekainc.com/a&boutus/companyoverview.html). Alternatively, the monoclonal antibodies of the present invention can be produced in yeasts or filamentous fungi engineered for mammalian-like glycosylation pattern and capable of producing antibodies lacking fucose as glycosylation pattern (see for example EP1297172B1).

Half Life

In one embodiment, the antibody is modified to increase its biological half-life. Various approaches are possible. For example, one or more of the following mutations can be introduced: T252L, T254S, T256F, as described in U.S. Pat. No. 6,277,375 by Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al. Antibodies with increased half lives and improved binding to the neonatal Fc receptor (FcRn), which is responsible for the transfer of maternal IgGs to the foetus (Guyer et al., J. Immunol. 117:587 (1976)

and Kim et al., J. immunol. 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311,312, 317, 340, 356, 360, 362, 376, 378, 380, 382, 413, 424, or 434, e.g., substitutions of Fc region residue 434 (U.S. Pat. No. 7,371,826).

Another modification of the antibodies herein that is contemplated by the invention is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See for example, EP0154316 by Nishimura et al. and EP0401384 by Ishikawa et al.

Another modification of the antibodies that is contemplated by the invention is a conjugate or a protein fusion of at least the antigen-binding region of the antibody of the invention to serum protein, such as human serum albumin or a fragment thereof to increase half-life of the resulting molecule. Such approach is for example described in Ballance et al. EP0322094. Another possibility is a fusion of at least the antigen-binding region of the antibody of the invention to proteins capable of binding to serum proteins, such human serum albumin to increase half-life of the resulting molecule. Such approach is for example described in Nygren et al., EP 0 486 525.

Polysialylation is another technology, which uses the natural polymer polysialic acid (PSA) to prolong the active life and improve the stability of therapeutic peptides and proteins. PSA is a polymer of sialic acid (a sugar). When used for protein and therapeutic peptide drug delivery, polysialic acid provides a protective microenvironment on conjugation. This increases the active life of the therapeutic protein in the circulation and prevents it from being recognized by the immune system. The PSA polymer is naturally found in the human body. It was adopted by certain bacteria which evolved over millions of years to coat their walls with it. These naturally polysialylated bacteria were then able, by virtue of molecular mimicry, to foil the body's defense system. PSA, nature's ultimate stealth technology, can be easily produced from such bacteria in large quantities and with predetermined physical characteristics. Bacterial PSA is completely non-immunogenic, even when coupled to proteins, as it is chemically identical to PSA in the human body.

Another technology includes the use of hydroxyethyl starch ("HES") derivatives linked to antibodies. HES is a modified natural polymer derived from waxy maize starch and can be metabolized by the body's enzymes. HES solutions are usually administered to substitute deficient blood volume and to improve the rheological properties of the blood. Hesylation of an antibody enables the prolongation of the circulation half-life by increasing the stability of the molecule, as well as by reducing renal clearance, resulting in an increased biological activity. By varying different parameters, such as the molecular weight of HES, a wide range of HES antibody conjugates can be customized.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

Others Modifications

In certain embodiments of the invention the antibodies have been engineered to increase pI and improve their drug-like properties. The pI of a protein is a key determinant of the overall biophysical properties of a molecule. Antibodies that have low pIs have been known to be less soluble, less stable, and prone to aggregation. Further, the purification of antibodies with low pI is challenging and can be problematic especially during scale-up for clinical use. Increasing the pI of the antibodies of the invention or fragments thereof improved their solubility, enabling the antibodies to be formulated at higher concentrations (>100 mg/ml). Formulation of the antibodies at high concentrations (e.g. >100 mg/ml) offers the advantage of being able to administer higher doses of the antibodies into eyes of patients via intravitreal injections, which in turn may enable reduced dosing frequency, a significant advantage for treatment of chronic diseases including cardiovascular disorders. Higher pIs may also increase the FcRn-mediated recycling of the IgG version of the antibody thus enabling the drug to persist in the body for a longer duration, requiring fewer injections. Finally, the overall stability of the antibodies is significantly improved due to the higher pI resulting in longer shelf-life and bioactivity in vivo. Preferably, the pI is greater than or equal to 8.2.

CAR-T Cells Comprising an Antigen Binding Domain of the Antibody of the Invention The present invention also provides chimeric antigen receptors (CARs) comprising an antigen binding domain of the antibody of the present invention. Typically, said chimeric antigen receptor comprises at least one VH and/or VL sequence of the antibody of the present invention. The chimeric antigen receptor of the present invention also comprises an extracellular hinge domain, a transmembrane domain, and an intracellular T cell signaling domain.

As used herein, the term "chimeric antigen receptor" or "CAR" has its general meaning in the art and refers to an artificially constructed hybrid protein or polypeptide containing the antigen binding domains of an antibody (e.g., scFv) linked to T-cell signaling domains. Characteristics of CARs include their ability to redirect T-cell specificity and reactivity toward a selected target in a non-MHC-restricted manner, exploiting the antigen-binding properties of monoclonal antibodies. The non-MHC-restricted antigen recognition gives T cells expressing CARs the ability to recognize antigen independent of antigen processing, thus bypassing a major mechanism of tumor escape. Moreover, when expressed in T-cells, CARs advantageously do not dimerize with endogenous T cell receptor (TCR) alpha and beta chains.

In some embodiments, the invention provides CARs comprising an antigen-binding domain comprising, consisting of, or consisting essentially of, a single chain variable fragment (scFv) of the antibody of the invention. In some embodiments, the antigen binding domain comprises a linker peptide. The linker peptide may be positioned between the light chain variable region and the heavy chain variable region.

In some embodiments, the CAR comprises an extracellular hinge domain, a transmembrane domain, and an intracellular T cell signaling domain selected from the group consisting of CD28, 4-1BB, and CD3ζ intracellular domains. CD28 is a T cell marker important in T cell co-stimulation. 4-1BB transmits a potent costimulatory signal to T cells, promoting differentiation and enhancing long-term survival of T lymphocytes. CD3ζ associates with TCRs to produce a signal and contains immunoreceptor tyrosine-based activation motifs (ITAMs).

In some embodiments, the chimeric antigen receptor of the present invention can be glycosylated, amidated, carboxylated, phosphorylated, esterified, N-acylated, cyclized via, e.g., a disulfide bridge, or converted into an acid addition salt and/or optionally dimerized or polymerized.

The invention also provides a nucleic acid encoding for a chimeric antigen receptor of the present invention. In some embodiments, the nucleic acid is incorporated in a vector as such as described above.

The present invention also provides a host cell comprising a nucleic acid encoding for a chimeric antigen receptor of the present invention. The host cell can be of any cell type, can originate from any type of tissue, and can be of any developmental stage. In one embodiment, the host cell is a T cell, e.g. isolated from peripheral blood lymphocytes (PBL) or peripheral blood mononuclear cells (PBMC). In some embodiments, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. The T cell can be any type of T cell and can be of any developmental stage, including but not limited to, CD4+/CD8+ double positive T cells, CD4+ helper T cells, e.g., Th2 cells, CD8+ T cells (e.g., cytotoxic T cells), tumor infiltrating cells, memory T cells, naive T cells, and the like. The T cell may be a CD8+ T cell or a CD4+ T cell.

The population of those T cells prepared as described above can be utilized in methods and compositions for adoptive immunotherapy in accordance with known techniques, or variations thereof that will be apparent to those skilled in the art based on the instant disclosure. See, e.g., US Patent Application Publication No. 2003/0170238 to Gruenberg et al; see also U.S. Pat. No. 4,690,915 to Rosenberg. Adoptive immunotherapy of cancer refers to a therapeutic approach in which immune cells with an antitumor reactivity are administered to a tumor-bearing host, with the aim that the cells mediate either directly or indirectly, the regression of an established tumor. Transfusion of lymphocytes, particularly T lymphocytes, falls into this category. Currently, most adoptive immunotherapies are based on autologous tumor-infiltrating lymphocytes (TIL) directed to treatments using the patient's own immune cells. These therapies involve processing the patient's own lymphocytes to either enhance the immune cell mediated response or to recognize specific antigens or foreign substances in the body, including the cancer cells. The treatments are accomplished by removing the patient's lymphocytes and exposing these cells in vitro to biologics and drugs to activate the immune function of the cells. Once the autologous cells are activated, these ex vivo activated cells are reinfused into the patient to enhance the immune system to treat cancer. In some embodiments, the cells are formulated by first harvesting them from their culture medium, and then washing and concentrating the cells in a medium and container system suitable for administration (a "pharmaceutically acceptable" carrier) in a treatment-effective amount. Suitable infusion medium can be any isotonic medium formulation, typically normal saline, Normosol R (Abbott) or Plasma-Lyte A (Baxter), but also 5% dextrose in water or Ringer's lactate can be utilized. The infusion medium can be supplemented with human serum albumin. A treatment-effective amount of cells in the composition is dependent on the relative representation of the T cells with the desired specificity, on the age and weight of the recipient, on the severity of the targeted condition and on the immunogenicity of the targeted Ags. These amount of cells can be as low as approximately $10^3$/kg, preferably $5 \times 10^3$/kg; and as high as $10^7$/kg, preferably $10^8$/kg. The number of cells will depend upon the ultimate use for which the composition is intended, as will the type of cells included therein. For example, if cells that are specific for a particular Ag are desired, then the population will contain greater than 70%, generally greater than 80%, 85% and 90-95% of such cells. For uses provided herein, the cells are generally in a volume of a liter or less, can be 500 ml or less, even 250 ml or 100 ml or less. The clinically relevant number of immune cells can be apportioned into multiple infusions that cumulatively equal or exceed the desired total amount of cells.

In particular the cells of the present invention are particularly suitable for the treatment of cancer. According, a further object of the present invention relates to a method of treating cancer in a subject in need thereof comprising administering to the subject a therapeutically effective amount of a population of cells of the present invention.

Multispecific Antibodies

In some embodiments, the invention provides a multispecific antibody comprising a first antigen binding site from an antibody of the present invention molecule described herein above and at least one second antigen binding site.

In some embodiments, the second antigen-binding site is used for recruiting a killing mechanism such as, for example, by binding an antigen on a human effector cell as a BiTE (Bispecific T-Cell engager) antibody which is a bispecific scFv2 directed against target antigen and CD3 on T cells described in U.S. Pat. No. 7,235,641, or by binding a cytotoxic agent or a second therapeutic agent. As used herein, the term "effector cell" refers to an immune cell which is involved in the effector phase of an immune response, as opposed to the cognitive and activation phases of an immune response. Exemplary immune cells include a cell of a myeloid or lymphoid origin, for instance lymphocytes (such as B cells and T cells including cytolytic T cells (CTLs)), killer cells, natural killer cells, macrophages, monocytes, mast cells and granulocytes, such as neutrophils, eosinophils and basophils. Some effector cells express specific Fc receptors (FcRs) and carry out specific immune functions. In some embodiments, an effector cell is capable of inducing ADCC, such as a natural killer cell. For example, monocytes, macrophages, which express FcRs, are involved in specific killing of target cells and presenting antigens to other components of the immune system. In some embodiments, an effector cell may phagocytose a target antigen or target cell. The expression of a particular FcR on an effector cell may be regulated by humoral factors such as cytokines. An effector cell can phagocytose a target antigen or phagocytose or lyse a target cell. Suitable cytotoxic agents and second therapeutic agents are exemplified below, and include toxins (such as radiolabeled peptides), chemotherapeutic agents and prodrugs.

In some embodiments, the second antigen-binding site binds to an antigen on Tumor Associated Macrophage, such as, e.g., CD163, CD204, CD206, CD68 and Tim-3.

As used herein, the term "CD68" (Cluster of Differentiation 68) also known as "GP110"; "LAMP4" and "SCARD1" has its general meaning in the art and refers to a protein that in humans is encoded by the CD68 gene.[Gene ID: 968]. This gene encodes a 110-kD transmembrane glycoprotein that is highly expressed by human monocytes and tissue macrophages. It is a member of the lysosomal/endosomal-associated membrane glycoprotein (LAMP) family. The protein primarily localizes to lysosomes and endosomes with a smaller fraction circulating to the cell surface. It is a type I integral membrane protein with a heavily glycosylated extracellular domain and binds to tissue- and organ-specific lectins or selectins. The protein is also a member of the scavenger receptor family. Scavenger receptors typically function to clear cellular debris, promote phagocytosis, and mediate the recruitment and activation of macrophages.

As used herein, the term "CD163" (Cluster of Differentiation 163) also known as "M130"; "MM130"; "SCAR11" has its general meaning in the art and refers to a protein that in humans is encoded by the CD163 gene.[Gene ID: 9332] CD163 is exclusively expressed in monocytes and macrophages. It functions as an acute phase-regulated receptor involved in the clearance and endocytosis of hemoglobin/haptoglobin complexes by macrophages, and may thereby protect tissues from free hemoglobin-mediated oxidative damage. This protein may also function as an innate immune sensor for bacteria and inducer of local inflammation. The molecular size is 130 kDa. The receptor belongs to the scavenger receptor cysteine rich family type B and consists of an 1048 amino acid residues extracellular domain, a single transmembrane segment and a cytoplasmic tail with several splice variants.

As used herein, the term "CD204" (Cluster of Differentiation 204) also known as "Macrophage scavenger receptor 1" (MSR1) has its general meaning in the art and refers to a protein that in humans is encoded by the MSR1 gene (NCBI reference: mRNA sequence: NM_138716). The Uniprot reference of CD204 is P21757 and the NCBI reference protein sequence is NP_002436.

As used herein, the term "CD206" (Cluster of Differentiation 206) also known as "mannose receptor" has its general meaning in the art and refers to a C-type lectin primarily present on the surface of macrophages and immature dendritic cells, but also expressed on the surface of skin cells such as human dermal fibroblasts and keratinocytes. The uniprot reference of CD206 is P22897.

As used herein, the term "Tim-3" also known as "Hepatitis A virus cellular receptor 2" (HAVCR2) has its general meaning in the art and refers to T-cell immunoglobulin and mucin-domain containing-3 that in humans is encoded by the HAVCR2 gene (NCBI reference: mRNA sequence: NM_032782). The Uniprot reference of Tim-3 is Q8TDQ0 and the NCBI reference protein sequence is NP_116171.

Exemplary formats for the multispecific antibody molecules of the invention include, but are not limited to (i) two antibodies cross-linked by chemical heteroconjugation, one with a specificity to sideroflexin-3 and another with a specificity to a second antigen; (ii) a single antibody that comprises two different antigen-binding regions; (iii) a single-chain antibody that comprises two different antigen-binding regions, e.g., two scFvs linked in tandem by an extra peptide linker; (iv) a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In: Antibody Engineering, Springer Berlin Heidelberg (2010)); (v) a chemically-linked bispecific (Fab')2 fragment; (vi) a Tandab, which is a fusion of two single chain diabodies resulting in a tetravalent bispecific antibody that has two binding sites for each of the target antigens; (vii) a flexibody, which is a combination of scFvs with a diabody resulting in a multivalent molecule; (viii) a so called "dock and lock" molecule, based on the "dimerization and docking domain" in Protein Kinase A, which, when applied to Fabs, can yield a trivalent bispecific binding protein consisting of two identical Fab fragments linked to a different Fab fragment; (ix) a so-called Scorpion molecule, comprising, e.g., two scFvs fused to both termini of a human Fab-arm; and (x) a diabody. Another exemplary format for bispecific antibodies is IgG-like molecules with complementary CH3 domains to force heterodimerization. Such molecules can be prepared using known technologies, such as, e.g., those known as Triomab/Quadroma (Trion Pharma/Fresenius Biotech), Knob-into-Hole (Genentech), CrossMAb (Roche) and electrostatically-matched (Amgen), LUZ-Y (Genentech), Strand Exchange Engineered Domain body (SEEDbody)(EMD Serono), Biclonic (Merus) and DuoBody (Genmab A/S) technologies.

In some embodiments, the bispecific antibody is obtained or obtainable via a controlled Fab-arm exchange, typically using DuoBody technology. In vitro methods for producing bispecific antibodies by controlled Fab-arm exchange have been described in WO2008119353 and WO 2011131746 (both by Genmab A/S). In one exemplary method, described in WO 2008119353, a bispecific antibody is formed by "Fab-arm" or "half-molecule" exchange (swapping of a heavy chain and attached light chain) between two monospecific antibodies, both comprising IgG4-like CH3 regions, upon incubation under reducing conditions. The resulting product is a bispecific antibody having two Fab arms which may comprise different sequences. In another exemplary method, described in WO 2011131746, bispecific antibodies of the present invention are prepared by a method comprising the following steps, wherein at least one of the first and second antibodies is the antibody of the present invention: a) providing a first antibody comprising an Fc region of an immunoglobulin, said Fc region comprising a first CH3 region; b) providing a second antibody comprising an Fc region of an immunoglobulin, said Fc region comprising a second CH3 region; wherein the sequences of said first and second CH3 regions are different and are such that the heterodimeric interaction between said first and second CH3 regions is stronger than each of the homodimeric interactions of said first and second CH3 regions; c) incubating said first antibody together with said second antibody under reducing conditions; and d) obtaining said bispecific antibody, wherein the first antibody is the antibody of the present invention and the second antibody has a different binding specificity, or vice versa. The reducing conditions may, for example, be provided by adding a reducing agent, e.g. selected from 2-mercaptoethylamine, dithiothreitol and tris(2-carboxyethyl)phosphine. Step d) may further comprise restoring the conditions to become non-reducing or less reducing, for example by removal of a reducing agent, e.g. by desalting. Preferably, the sequences of the first and second CH3 regions are different, comprising only a few, fairly conservative, asymmetrical mutations, such that the heterodimeric interaction between said first and second CH3 regions is stronger than each of the homodimeric interactions of said first and second CH3 regions. More details on these interactions and how they can be achieved are provided in WO 2011131746, which is hereby incorporated by reference in its entirety. The following are exemplary embodiments of combinations of such assymetrical mutations, optionally wherein one or both Fc-regions are of the IgG1 isotype.

Immunoconjugates

Detectable Label

An antibody of the invention can be conjugated with a detectable label to form an immunoconjugate. Suitable detectable labels include, for example, a radioisotope, a fluorescent label, a chemiluminescent label, an enzyme label, a bioluminescent label or colloidal gold. Methods of making and detecting such detectably-labeled immunoconjugates are well-known to those of ordinary skill in the art, and are described in more detail below. The detectable label can be a radioisotope that is detected by autoradiography. Isotopes that are particularly useful for the purpose of the invention are 3H, 125I, 131I, 35S and 14C.

Immunoconjugates can be labeled with a fluorescent compound. The presence of a fluorescently-labeled antibody is determined by exposing the immunoconjugate to light of the proper wavelength and detecting the resultant fluorescence. Fluorescent labeling compounds include fluorescein isothiocyanate, rhodamine, phycoerytherin, phycocyanin, allophycocyanin, o-phthaldehyde and fluorescamine.

Alternatively, immunoconjugates can be detectably labeled by coupling an antibody to a chemiluminescent compound. The presence of the chemiluminescent-tagged immunoconjugate is determined by detecting the presence of luminescence that arises during the course of a chemical reaction. Examples of chemiluminescent labeling compounds include luminol, isoluminol, an aromatic acridinium ester, an imidazole, an acridinium salt and an oxalate ester.

Similarly, a bioluminescent compound can be used to label immunoconjugates of the invention. Bioluminescence is a type of chemiluminescence found in biological systems in which a catalytic protein increases the efficiency of the chemiluminescent reaction. The presence of a bioluminescent protein is determined by detecting the presence of luminescence. Bioluminescent compounds that are useful for labeling include luciferin, luciferase and aequorin.

Alternatively, immunoconjugates can be detectably labeled by linking an antibody of the invention to an enzyme. When the antibody-enzyme conjugate is incubated in the presence of the appropriate substrate, the enzyme moiety reacts with the substrate to produce a chemical moiety which can be detected, for example, by spectrophotometric, fluorometric or visual means. Examples of enzymes that can be used to detectably label polyspecific immunoconjugates include β-galactosidase, glucose oxidase, peroxidase and alkaline phosphatase.

Those of skill in the art will know of other suitable labels which can be employed in accordance with the invention. The binding of marker moieties to antibodies can be accomplished using standard techniques known to the art. Typical methodology in this regard is described by Kennedy et al., Clin. Chim. Acta 70:1, 1976; Schurs et al., Clin. Chim. Acta 81:1, 1977; Shih et al., Intl J. Cancer 46:1101, 1990; Stein et al., Cancer Res. 50:1330, 1990; and Coligan.

Moreover, the convenience and versatility of immunochemical detection can be enhanced by using antibodies that have been conjugated with avidin, streptavidin, and biotin. (See, e.g., Wilchek et al. (eds.), "Avidin-Biotin Technology," Methods In Enzymology (Vol. 184) (Academic Press 1990); Bayer et al., "Immunochemical Applications of Avidin-Biotin Technology," in Methods In Molecular Biology (Vol. 10) 149-162 (Manson, ed., The Humana Press, Inc. 1992)).

Methods for performing immunoassays are well-established. (See, e.g., Cook and Self, "Monoclonal Antibodies in Diagnostic Immunoassays," in Monoclonal Antibodies: Production, Engineering, and Clinical Application 180-208 (Ritter and Ladyman, eds., Cambridge University Press 1995); Perry, "The Role of Monoclonal Antibodies in the Advancement of Immunoassay Technology," in Monoclonal Antibodies: Principles and Applications 107-120 (Birch and Lennox, eds., Wiley-Liss, Inc. 1995); Diamandis, Immunoassay (Academic Press, Inc. 1996)).

Antibody-Drug Conjugates (ADC)

In some embodiments, the antibody of the present invention is conjugated to a therapeutic moiety, i.e. a drug. The therapeutic moiety can be, e.g., a cytotoxin, a chemotherapeutic agent, a cytokine, an immunosuppressant, an immune stimulator, a lytic peptide, or a radioisotope. Such conjugates are referred to herein as an "antibody-drug conjugates" or "ADCs".

In some embodiments, the antibody is conjugated to a cytotoxic moiety. The cytotoxic moiety may, for example, be selected from the group consisting of taxol; cytochalasin B; gramicidin D; ethidium bromide; emetine; mitomycin; etoposide; tenoposide; vincristine; vinblastine; colchicin; doxorubicin; daunorubicin; dihydroxy anthracin dione; a tubulin-inhibitor such as maytansine or an analog or derivative thereof; an antimitotic agent such as monomethyl auristatin E or F or an analog or derivative thereof; dolastatin 10 or 15 or an analogue thereof; irinotecan or an analogue thereof; mitoxantrone; mithramycin; actinomycin D; 1-dehydrotestosterone; a glucocorticoid; procaine; tetracaine; lidocaine; propranolol; puromycin; calicheamicin or an analog or derivative thereof; an antimetabolite such as methotrexate, 6 mercaptopurine, 6 thioguanine, cytarabine, fludarabin, 5 fluorouracil, decarbazine, hydroxyurea, asparaginase, gemcitabine, or cladribine; an alkylating agent such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C; a platinum derivative such as cisplatin or carboplatin; duocarmycin A, duocarmycin SA, rachelmycin (CC-1065), or an analog or derivative thereof; an antibiotic such as dactinomycin, bleomycin, daunorubicin, doxorubicin, idarubicin, mithramycin, mitomycin, mitoxantrone, plicamycin, anthramycin (AMC)); pyrrolo[2,1-c][1,4]-benzodiazepines (PDB); diphtheria toxin and related molecules such as diphtheria A chain and active fragments thereof and hybrid molecules, ricin toxin such as ricin A or a deglycosylated ricin A chain toxin, cholera toxin, a Shiga-like toxin such as SLT I, SLT II, SLT IIV, LT toxin, C3 toxin, Shiga toxin, pertussis toxin, tetanus toxin, soybean Bowman-Birk protease inhibitor, *Pseudomonas* exotoxin, alorin, saporin, modeccin, gelanin, abrin A chain, modeccin A chain, alpha-sarcin, *Aleurites fordii* proteins, dianthin proteins, *Phytolacca americana* proteins such as PAPI, PAPII, and PAP-S, *Momordica charantia* inhibitor, curcin, crotin, *Sapaonaria officinalis* inhibitor, gelonin, mitogellin, restrictocin, phenomycin, and enomycin toxins; ribonuclease (RNase); DNase I, Staphylococcal enterotoxin A; pokeweed antiviral protein; diphtherin toxin; and *Pseudomonas* endotoxin.

In some embodiments, the antibody is conjugated to a nucleic acid or nucleic acid-associated molecule. In one such embodiment, the conjugated nucleic acid is a cytotoxic ribonuclease (RNase) or deoxy-ribonuclease (e.g., DNase I), an antisense nucleic acid, an inhibitory RNA molecule (e.g., a siRNA molecule) or an immunostimulatory nucleic acid (e.g., an immunostimulatory CpG motif-containing DNA molecule). In some embodiments, the antibody is conjugated to an aptamer or a ribozyme.

In some embodiments, the antibody is conjugated, e.g., as a fusion protein, to a lytic peptide such as CLIP, Magainin 2, mellitin, Cecropin and P18.

In some embodiments, the antibody is conjugated to a cytokine, such as, e.g., IL-2, IL-4, IL-6, IL-7, IL-10, IL-12, IL-13, IL-15, IL-18, IL-23, IL-24, IL-27, IL-28a, IL-28b, IL-29, KGF, IFNa, IFN3, IFNy, GM-CSF, CD40L, Flt3 ligand, stem cell factor, ancestim, and TNFa.

In some embodiments, the antibody is conjugated to a radioisotope or to a radioisotope-containing chelate. For example, the antibody can be conjugated to a chelator linker, e.g. DOTA, DTPA or tiuxetan, which allows for the antibody to be complexed with a radioisotope. The antibody may also or alternatively comprise or be conjugated to one or more radiolabeled amino acids or other radiolabeled molecules. Non-limiting examples of radioisotopes include 3H, 14C, 15N, 35S, 90Y, 99Tc, 125I, 131I, 186Re, 213Bi, 225Ac and 227Th. For therapeutic purposes, a radioisotope emitting beta- or alpha-particle radiation can be used, e.g., 131I, 90Y, 211At, 212Bi, 67Cu, 186Re, 188Re, and 212Pb.

In certain embodiments, an antibody-drug conjugate comprises an anti-tubulin agent. Examples of anti-tubulin agents include, for example, taxanes (e.g., Taxol® (paclitaxel), Taxotere® (docetaxel)), T67 (Tularik), vinca alkyloids (e.g., vincristine, vinblastine, vindesine, and vinorelbine), and dolastatins (e.g., auristatin E, AFP, MMAF, MMAE, AEB, AEVB). Other antitubulin agents include, for example, baccatin derivatives, taxane analogs (e.g., epothilone A and B), nocodazole, colchicine and colcimid, estramustine, cryptophysins, cemadotin, maytansinoids, combretastatins, discodermolide, and eleutherobin. In some embodiments, the cytotoxic agent is a maytansinoid, another group of anti-tubulin agents. For example, in specific embodiments, the maytansinoid is maytansine or DM-1 (ImmunoGen, Inc.; see also Chari et al., Cancer Res. 52:127-131, 1992).

In other embodiments, the cytotoxic agent is an antimetabolite. The antimetabolite can be, for example, a purine antagonist (e.g., azothioprine or mycophenolate mofetil), a dihydrofolate reductase inhibitor (e.g., methotrexate), acyclovir, gangcyclovir, zidovudine, vidarabine, ribavarin, azidothymidine, cytidine arabinoside, amantadine, dideoxyuridine, iododeoxyuridine, poscarnet, or trifluridine.

In other embodiments, the antibody of the invention is conjugated to a pro-drug converting enzyme. The pro-drug converting enzyme can be recombinantly fused to the antibody or chemically conjugated thereto using known methods. Exemplary pro-drug converting enzymes are carboxypeptidase G2, β-glucuronidase, penicillin-V-amidase, penicillin-G-amidase, β-lactamase, β-glucosidase, nitroreductase and carboxypeptidase A.

Diagnostic Uses

As described in the experimental section, the antibody of the present invention permits the detection of Tumor Associated Macrophages, and so the detection of the tumor microenvironment involved in cancers.

An aspect of the present invention relates to the use of the antibody of the present invention for detecting Tumor Associated Macrophages.

Accordingly, an aspect of the present invention relates to a method for detecting Tumor Associated Macrophages, and/or evaluating its amount in a biological sample, wherein said method comprises contacting said sample with an antibody of the invention. In one embodiment, the method is used for the diagnosis of cancers.

A further aspect of the invention relates to an antibody of the invention for diagnosing cancer disease and other diseases in which sideroflexin-3 levels are modified (increased or decreased).

In a preferred embodiment, antibodies of the invention may be labelled with a detectable molecule or substance, such as a fluorescent molecule, a radioactive molecule or any others labels known in the art as above described. For example, an antibody of the invention may be labelled with a radioactive molecule by any method known to the art. For example radioactive molecules include but are not limited radioactive atom for scintigraphic studies such as I123, I124, In111, Re186, Re188. Antibodies of the invention may be also labelled with a spin label for nuclear magnetic resonance (NMR) imaging (also known as magnetic resonance imaging, MRI), such as iodine-123, iodine-131, indium-111, fluorine-19, carbon-13, nitrogen-15, oxygen-17, gadolinium, manganese or iron. Following administration of the antibody, the distribution of the antibody within the patient is detected. Methods for detecting distribution of any specific label are known to those skilled in the art and any appropriate method can be used. Some non-limiting examples include, computed tomography (CT), position emission tomography (PET), magnetic resonance imaging (MRI), fluorescence, chemiluminescence and sonography.

Antibodies of the invention may be useful for diagnosing and staging of cancer diseases associated with Tumor Associated Macrophages.

Typically, said diagnostic methods involve use of biological sample obtained from the patient. As used herein the term "biological sample" encompasses a variety of sample types obtained from a subject and can be used in a diagnostic or monitoring assay. Biological samples include but are not limited to blood and other liquid samples of biological origin, solid tissue samples such as a biopsy specimen or tissue cultures or cells derived therefrom, and the progeny thereof. For example, biological samples include cells obtained from a tissue sample collected from an individual suspected of having a cancer disease associated with Tumor Associated Macrophages.

Biological samples encompass clinical samples, cells in culture, cell supernatants, cell lysates, serum, plasma, biological fluid, and tissue samples.

Therapeutic Uses

As described in the experimental section, the antibody of the present invention targets Tumor Associated Macrophages, which are involved in the tumor microenvironment in cancers. The tumor microenvironment is recognized to play a very important role in promoting cancer initiation and tumor growth.

Antibodies, fragments or immunoconjugates of the invention may be useful for treating any disease associated with Tumor Associated Macrophages preferentially cancers. The antibodies of the invention may be used alone or in combination with any suitable agent.

In each of the embodiments of the treatment methods described herein, the antibody of the invention or antibody-drug conjugate of the invention is delivered in a manner consistent with conventional methodologies associated with management of the disease or disorder for which treatment is sought. In accordance with the disclosure herein, an effective amount of the antibody or antibody-drug conjugate is administered to a patient in need of such treatment for a time and under conditions sufficient to prevent or treat the disease or disorder.

As used herein, the term "treatment" or "treat" refer to both prophylactic or preventive treatment as well as curative or disease modifying treatment, including treatment of subjects at risk of contracting the disease or suspected to have contracted the disease as well as subjects who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a subject during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a subject during treatment of an illness, e.g., to keep the subject in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

As used herein, the term "therapeutically effective amount" or "effective amount" refers to an amount effective, at dosages and for periods of time necessary, to achieve a desired therapeutic result. A therapeutically effective amount of the antibody of the present invention may vary according to factors such as the disease state, age, sex, and weight of the individual, and the ability of the antibody of the present invention to elicit a desired response in the individual. A therapeutically effective amount is also one in which any toxic or detrimental effects of the antibody or antibody portion are outweighed by the therapeutically beneficial effects. The efficient dosages and dosage regimens for the antibody of the present invention depend on the disease or condition to be treated and may be determined by the persons skilled in the art. A physician having ordinary skill in the art may readily determine and prescribe the effective amount of the pharmaceutical composition required. For example, the physician could start doses of the antibody of the present invention employed in the pharmaceutical composition at levels lower than that required in order to achieve the desired therapeutic effect and gradually increase the dosage until the desired effect is achieved. In general, a suitable dose of a composition of the present invention will be that amount of the compound which is the lowest dose effective to produce a therapeutic effect according to a particular dosage regimen. Such an effective dose will generally depend upon the factors described above. For example, a therapeutically effective amount for therapeutic use may be measured by its ability to stabilize the progression of disease. Typically, the ability of a compound to inhibit cancer may, for example, be evaluated in an animal model system predictive of efficacy in human tumors. Alternatively, this property of a composition may be evaluated by examining the ability of the compound to induce cytotoxicity by in vitro assays known to the skilled practitioner. A therapeutically effective amount of a therapeutic compound may decrease tumor size, or otherwise ameliorate symptoms in a subject. One of ordinary skill in the art would be able to determine such amounts based on such factors as the subject's size, the severity of the subject's symptoms, and the particular composition or route of administration selected. An exemplary, non-limiting range for a therapeutically effective amount of an antibody of the present invention is about 0.1-100 mg/kg, such as about 0.1-50 mg/kg, for example about 0.1-20 mg/kg, such as about 0.1-10 mg/kg, for instance about 0.5, about such as 0.3, about 1, about 3 mg/kg, about 5 mg/kg or about 8 mg/kg. An exemplary, non-limiting range for a therapeutically effective amount of an antibody of the present invention is 0.02-100 mg/kg, such as about 0.02-30 mg/kg, such as about 0.05-10 mg/kg or 0.1-3 mg/kg, for example about 0.5-2 mg/kg. Administration may e.g. be intravenous, intramuscular, intraperitoneal, or subcutaneous, and for instance administered proximal to the site of the target. Dosage regimens in the above methods of treatment and uses are adjusted to provide the optimum desired response (e.g., a therapeutic response). For example, a single bolus may be administered, several divided doses may be administered over time or the dose may be proportionally reduced or increased as indicated by the exigencies of the therapeutic situation. In some embodiments, the efficacy of the treatment is monitored during the therapy, e.g. at predefined points in time. In some embodiments, the efficacy may be monitored by visualization of the disease area, or by other diagnostic methods described further herein, e.g. by performing one or more PET-CT scans, for example using a labeled antibody of the present invention, fragment or mini-antibody derived from the antibody of the present invention. If desired, an effective daily dose of a pharmaceutical composition may be administered as two, three, four, five, six or more sub-doses administered separately at appropriate intervals throughout the day, optionally, in unit dosage forms. In some embodiments, the monoclonal antibodies of the present invention are administered by slow continuous infusion over a long period, such as more than 24 hours, in order to minimize any unwanted side effects. An effective dose of an antibody of the present invention may also be administered using a weekly, biweekly or triweekly dosing period. The dosing period may be restricted to, e.g., 8 weeks, 12 weeks or until clinical progression has been established. As non-limiting examples, treatment according to the present invention may be provided as a daily dosage of an antibody of the present invention in an amount of about 0.1-100 mg/kg, such as 0.2, 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of days 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of weeks 1, 2, 3, 4, 5, 6, 7, 8, 9, 10, 11, 12, 13, 14, 15, 16, 17, 18, 19 or 20 after initiation of treatment, or any combination thereof, using single or divided doses every 24, 12, 8, 6, 4, or 2 hours, or any combination thereof.

Accordingly, one object of the present invention relates to a method of treating cancers in a subject in need thereof comprising administering to the subject a therapeutically effective amount of an antibody of the present invention.

In another aspect, the present invention relates to the antibody of the present invention, as defined in any aspect or embodiment herein, for use as a medicament.

In another aspect, the present invention relates to the use of the antibody of the present invention for the treatment of cancers.

In certain embodiments, an antibody of the invention or antibody-drug conjugate is used in combination with a second agent for treatment of a disease or disorder. When used for treating cancer, an antibody of the invention or antibody-drug conjugate of the invention may be used in combination with conventional cancer therapies such as, e.g., surgery, radiotherapy, chemotherapy, or combinations thereof.

The terms "cancer" "malignancy" and "tumors" refer to or describe the pathological condition in mammals that is typically characterized by unregulated cell growth. More precisely, in the use of the invention, diseases, namely cancer are associated with Tumor-associated macrophages TAMs, which have been shown to be symbiotically related to tumor cells. Furthermore, inventors show that antagonist of the invention, like antibodies directed to sidoreflexin 3, kill Tumor-associated macrophages (TAMs) and decrease tumor cell growth: Tumor cells recruit TAMs which provide these with survival and angiogenic factors in the tumor microenvironment (see review Dirkx A. E. M. Journal of Leukocyte Biology vol. 80 no. 6 1183-1196 December 2006).

In particular, the cancer may be associated with a solid tumor or unregulated growth of undifferentiated bone marrow cells (i.e. leukemia, lymphoma).

A variety of cancers and other proliferative diseases including, but not limited to the following can be treated using the methods and compositions of the invention:

carcinoma, including that of the bladder, breast, uterine/cervical, colon, kidney, liver, lung, ovary, oesophage, pancreas, prostate, stomach, cervix, thyroid, colorectal, head and neck and skin, including squamous cell carcinoma, tumors of mesenchymal origin, including fibrosarcoma and rhabdomyoscarcoma;

other tumors, including melanoma, seminoma, teratocarcinoma, neuroblastoma and glioma;

tumors of the central and peripheral nervous system, including astrocytoma, neuroblastoma, glioma, and schwannomas;

tumors of mesenchymal origin, including fibrosarcoma, rhabdomyoscaroma, and osteosarcoma; and other tumors, including melanoma, xeroderma pigmentosum, keratoacarcinoma, seminoma, thyroid follicular cancer and teratocarcinoma.

lymphomas such as, but not limited to, Hodgkin's disease, non-Hodgkin's disease; multiple myelomas such as, but not limited to, smoldering multiple myeloma, non-secretory myeloma, osteosclerotic myeloma, plasma cell leukemia, solitary plasmacytoma and extramedullary plasmacytoma, Adult T-cell leukemia/lymphoma.

leukemias such as, but not limited to, acute leukemia, acute lymphocytic leukemia, acute myelocytic leukemias such as myeloblastic, promyelocytic, myelo-monocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia.

In one embodiment said cancer is a leukemia, which is selected from the group consisting of all acute and chronic leukemia: chronic lymphocytic leukemia (CLL), acute myelocytic leukemias (AML), acute lymphocytic leukemia (ALL), Adult T-cell leukemia/lymphoma (ATLL), Chronic myelomonocytic leukaemia (LMMC), Acute promyelocytic leukemia (APL).

In preferred embodiment said leukemia is chronic lymphocytic leukemia (CLL),

In one embodiment said cancer is a lymphoma which is selected from the group consisting of all non-Hodgkinien or Hodgkinien lymphomas, Adult T-cell leukemia/lymphoma (ATLL)

In one embodiment said cancer is a solid tumor selected from the group consisting of brain, head and neck, adrenal glands, colon, small intestines, stomach, heart, liver, skin, kidney, lung, pancreas, testis, ovary, prostate, uterus, thyroid, bladder, breast, endometrial tumors, multiple myeloma and sarcomas.

Where hereinbefore and subsequently a tumor, a tumor disease, a carcinoma or a cancer are mentioned, metastasis in the original organ or tissue and/or in any other location are implicitly meant alternatively or in addition, whatever the location of the tumor and/or metastasis is.

Combination

The present invention also provides for therapeutic applications where an antibody of the present invention is used in combination with at least one further therapeutic agent, e.g. for treating cancers. Such administration may be simultaneous, separate or sequential. For simultaneous administration the agents may be administered as one composition or as separate compositions, as appropriate. The further therapeutic agent is typically relevant for the disorder to be treated. Exemplary therapeutic agents include other anti-cancer antibodies, cytotoxic agents, chemotherapeutic agents, anti-angiogenic agents, anti-cancer immunogens, cell cycle control/apoptosis regulating agents, hormonal regulating agents, and other agents described below.

In some embodiments, the antibody of the present invention is used in combination with a chemotherapeutic agent. The term "chemotherapeutic agent" refers to chemical compounds that are effective in inhibiting tumor growth. Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaorarnide and trimethylolomelamine; acetogenins (especially bullatacin and bullatacinone); a carnptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estrarnustine, ifosfamide, mechlorethamine, mechlorethamine oxide hydrochloride, melphalan, novembichin, phenesterine, prednimus tine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin (11 and calicheamicin 211, see, e.g., Agnew Chem Intl. Ed. Engl. 33:183-186 (1994); dynemicin, including dynemicin A; an esperamicin; as well as neocarzinostatin chromophore and related chromoprotein enediyne antiobiotic chromomophores), aclacinomysins, actinomycin, authramycin, azaserine, bleomycins, cactinomycin, carabicin, canninomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idanrbicin, marcellomycin, mitomycins, mycophenolic acid, nogalarnycin, olivomycins, peplomycin, potfiromycin, puromycin, quelamycin, rodorubicin, streptomgrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophospharnide glycoside; aminolevulinic acid; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pento statin; phenamet; pirarubicin; podophyllinic acid; 2-ethylhydrazide; procarbazine; PSK®; razoxane; rhizoxin; sizofiran; spirogennanium; tenuazonic acid; triaziquone; 2,2',2"-trichlorotriethylarnine; trichothecenes (especially T-2 toxin, verracurin A, roridinA and anguidine); urethan; vindesine; dacarbazine; mannomustine; mitobromtol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.].) and doxetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-1 1; topoisomerase inhibitor RFS 2000; difluoromethylornithine (DMFO); retinoic acid; capecitabine; and pharmaceutically acceptable salts, acids or derivatives of any of the above. Also included in this definition are antihormonal agents that act to regulate or inhibit honnone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

In some embodiments, the antibody of the present invention is used in combination with a targeted cancer therapy. Targeted cancer therapies are drugs or other substances that block the growth and spread of cancer by interfering with specific molecules ("molecular targets") that are involved in the growth, progression, and spread of cancer. Targeted cancer therapies are sometimes called "molecularly targeted drugs," "molecularly targeted therapies," "precision medicines," or similar names. In some embodiments, the targeted therapy consists of administering the subject with a tyrosine kinase inhibitor. The term "tyrosine kinase inhibitor" refers to any of a variety of therapeutic agents or drugs that act as selective or non-selective inhibitors of receptor and/or non-receptor tyrosine kinases. Tyrosine kinase inhibitors and related compounds are well known in the art and described in U.S Patent Publication 2007/0254295, which is incorporated by reference herein in its entirety. It will be appreciated by one of skill in the art that a compound related to a tyrosine kinase inhibitor will recapitulate the effect of the tyrosine kinase inhibitor, e.g., the related compound will act on a different member of the tyrosine kinase signaling pathway to produce the same effect as would a tyrosine kinase inhibitor of that tyrosine kinase. Examples of tyrosine kinase inhibitors and related compounds suitable for use in methods of embodiments of the present invention include, but are not limited to, dasatinib (BMS-354825), PP2, BEZ235, saracatinib, gefitinib (Iressa), sunitinib (Sutent; SU11248), erlotinib (Tarceva; OSI-1774), lapatinib (GW572016; GW2016), canertinib (CI 1033), semaxinib (SU5416), vatalanib (PTK787/ZK222584), sorafenib (BAY 43-9006), imatinib (Gleevec; STI571), leflunomide (SU101), vandetanib (Zactima; ZD6474), MK-2206 (8-[4-aminocyclobutyl)phenyl]-9-phenyl-1,2,4-triazolo[3,4-f][1,6]naphthyridin-3(2H)-one hydrochloride) derivatives thereof, analogs thereof, and combinations thereof. Additional tyrosine kinase inhibitors and related compounds suitable for use in the present invention are described in, for example, U.S Patent Publication 2007/0254295, U.S. Pat. Nos. 5,618,829, 5,639,757, 5,728,868, 5,804,396, 6,100,254, 6,127,374, 6,245,759, 6,306,874, 6,313,138, 6,316,444, 6,329,380, 6,344,459, 6,420,382, 6,479,512, 6,498,165, 6,544,988, 6,562,818, 6,586,423, 6,586,424, 6,740,665, 6,794,393, 6,875,767, 6,927,293, and 6,958,340, all of which are incorporated by reference herein in their entirety. In some embodiments, the tyrosine kinase inhibitor is a small molecule kinase inhibitor that has been orally administered and that has been the subject of at least one Phase I clinical trial, more preferably at least one Phase II clinical, even more preferably at least one Phase III clinical trial, and most preferably approved by the FDA for at least one hematological or oncological indication. Examples of such inhibitors include, but are not limited to, Gefitinib, Erlotinib, Lapatinib, Canertinib, BMS-599626 (AC-480), Neratinib, KRN-633, CEP-11981, Imatinib, Nilotinib, Dasatinib, AZM-475271, CP-724714, TAK-165, Sunitinib, Vatalanib, CP-547632, Vandetanib, Bosutinib, Lestaurtinib, Tandutinib, Midostaurin, Enzastaurin, AEE-788, Pazopanib, Axitinib, Motasenib, OSI-930, Cediranib, KRN-951, Dovitinib, Seliciclib, SNS-032, PD-0332991, MKC-I (Ro-317453; R-440), Sorafenib, ABT-869, Brivanib (BMS-582664), SU-14813, Telatinib, SU-6668, (TSU-68), L-21649, MLN-8054, AEW-541, and PD-0325901.

In some embodiments, the antibody of the present invention is used in combination with an immunotherapeutic agent. The term "immunotherapeutic agent," as used herein, refers to a compound, composition or treatment that indirectly or directly enhances, stimulates or increases the body's immune response against cancer cells and/or that decreases the side effects of other anticancer therapies. Immunotherapy is thus a therapy that directly or indirectly stimulates or enhances the immune system's responses to cancer cells and/or lessens the side effects that may have been caused by other anti-cancer agents. Immunotherapy is also referred to in the art as immunologic therapy, biological therapy biological response modifier therapy and biotherapy. Examples of common immunotherapeutic agents known in the art include, but are not limited to, cytokines, cancer vaccines, monoclonal antibodies and non-cytokine adjuvants. Alternatively the immunotherapeutic treatment may consist of administering the subject with an amount of immune cells (T cells, NK, cells, dendritic cells, B cells . . . ). Immunotherapeutic agents can be non-specific, i.e. boost the immune system generally so that the human body becomes more effective in fighting the growth and/or spread of cancer cells, or they can be specific, i.e. targeted to the cancer cells themselves immunotherapy regimens may combine the use of non-specific and specific immunotherapeutic agents. Non-specific immunotherapeutic agents are substances that stimulate or indirectly improve the immune system. Non-specific immunotherapeutic agents have been used alone as a main therapy for the treatment of cancer, as well as in addition to a main therapy, in which case the non-specific immunotherapeutic agent functions as an adjuvant to enhance the effectiveness of other therapies (e.g. cancer vaccines). Non-specific immunotherapeutic agents can also function in this latter context to reduce the side effects of other therapies, for example, bone marrow suppression induced by certain chemotherapeutic agents. Non-specific immunotherapeutic agents can act on key immune system cells and cause secondary responses, such as increased production of cytokines and immunoglobulins. Alternatively, the agents can themselves comprise cytokines. Non-specific immunotherapeutic agents are generally classified as cytokines or non-cytokine adjuvants. A number of cytokines have found application in the treatment of cancer either as general non-specific immunotherapies designed to boost the immune system, or as adjuvants provided with other therapies. Suitable cytokines include, but are not limited to, interferons, interleukins and colony-stimulating factors. Interferons (IFNs) contemplated by the present invention include the common types of IFNs, IFN-alpha (IFN-α), IFN-beta (IFN-β) and IFN-gamma (IFN-γ). IFNs can act directly on cancer cells, for example, by slowing their growth, promoting their development into cells with more normal behavior and/or increasing their production of antigens thus making the cancer cells easier for the immune system to recognise and destroy. IFNs can also act indirectly on cancer cells, for example, by slowing down angiogenesis, boosting the immune system and/or stimulating natural killer (NK) cells, T cells and macrophages. Recombinant IFN-alpha is available commercially as Roferon (Roche Pharmaceuticals) and Intron A (Schering Corporation). Interleukins contemplated by the present invention include IL-2, IL-4, IL-11 and IL-12. Examples of commercially available recombinant interleukins include Proleukin® (IL-2; Chiron Corporation) and Neumega® (IL-12; Wyeth Pharmaceuticals). Zymogenetics, Inc. (Seattle, Wash.) is currently testing a recombinant form of IL-21, which is also contemplated for use in the combinations of the present invention. Colony-stimulating factors (CSFs) contemplated by the present invention include granulocyte colony stimulating factor (G-CSF or filgrastim), granulocyte-macrophage colony stimulating factor (GM-CSF or sargramostim) and erythropoietin (epoetin alfa, darbepoietin). Treatment with one or more growth factors can help to stimulate the generation of new blood cells in subjects undergoing traditional chemotherapy. Accordingly, treatment with CSFs can be helpful in decreasing the side effects associated with chemotherapy and can allow for higher doses of chemotherapeutic agents to be used. Various-recombinant colony stimulating factors are available commercially, for example, Neupogen® (G-CSF; Amgen), Neulasta (pelfilgrastim; Amgen), Leukine (GM-CSF; Berlex), Procrit (erythropoietin; Ortho Biotech), Epogen (erythropoietin; Amgen), Arnesp (erytropoietin). Combination compositions and combination administration methods of the present invention may also involve "whole cell" and "adoptive" immunotherapy methods. For instance, such methods may comprise infusion or re-infusion of immune system cells (for instance tumor-infiltrating lymphocytes (TILs), such as CC2+ and/or CD8+ T cells (for instance T cells expanded with tumor-specific antigens and/or genetic enhancements), antibody-expressing B cells or other antibody-producing or -presenting cells, dendritic cells (e.g., dendritic cells cultured with a DC-expanding agent such as GM-CSF and/or Flt3-L, and/or tumor-associated antigen-loaded dendritic cells), anti-tumor NK cells, so-called hybrid cells, or combinations thereof. Cell lysates may also be useful in such methods and compositions. Cellular "vaccines" in clinical trials that may be useful in such aspects include Canvaxin™, APC-8015 (Dendreon), HSPPC-96 (Antigenics), and Melacine® cell lysates. Antigens shed from cancer cells, and mixtures thereof (see for instance Bystryn et al., Clinical Cancer Research Vol. 7, 1882-1887, July 2001), optionally admixed with adjuvants such as alum, may also be components in such methods and combination compositions.

In some embodiments, the antibody of the present invention is used in combination with radiotherapy. Radiotherapy may comprise radiation or associated administration of radiopharmaceuticals to a patient. The source of radiation may be either external or internal to the patient being treated (radiation treatment may, for example, be in the form of external beam radiation therapy (EBRT) or brachytherapy (BT)). Radioactive elements that may be used in practicing such methods include, e.g., radium, cesium-137, iridium-192, americium-241, gold-198, cobalt-57, copper-67, technetium-99, iodide-123, iodide-131, and indium-111.

In some embodiments, the antibody of the present invention is used in combination with an antibody that is specific for a costimulatory molecule. Examples of antibodies that are specific for a costimulatory molecule include but are not limited to anti-CTLA4 antibodies (e.g. Ipilimumab), anti-PD1 antibodies, anti-PDLL antibodies, anti-TIMP3 antibodies, anti-LAG3 antibodies, anti-B7H3 antibodies, anti-B7H4 antibodies or anti-B7H6 antibodies.

A further object of the present invention relates to a method of treating cancer in a subject in need thereof comprising administering to the subject a first antibody selective for a cancer cell antigen, and administering to the subject an antibody of the present invention.

A number of antibodies are currently in clinical use for the treatment of cancer, and others are in varying stages of clinical development. Antibodies of interest for the methods of the invention act through ADCC, and are typically selective for tumor cells, although one of skill in the art will recognize that some clinically useful antibodies do act on non-tumor cells, e.g. CD20. There are a number of antigens and corresponding monoclonal antibodies for the treatment of B cell malignancies. One popular target antigen is CD20, which is found on B cell malignancies. Rituximab is a chimeric unconjugated monoclonal antibody directed at the CD20 antigen. CD20 has an important functional role in B cell activation, proliferation, and differentiation. The CD52 antigen is targeted by the monoclonal antibody alemtuzumab, which is indicated for treatment of chronic lymphocytic leukemia. CD22 is targeted by a number of antibodies, and has recently demonstrated efficacy combined with toxin in chemotherapy-resistant hairy cell leukemia. Monoclonal antibodies targeting CD20, also include tositumomab and ibritumomab. Monoclonal antibodies useful in the methods of the invention, which have been used in solid tumors, include without limitation edrecolomab and trastuzumab (herceptin). Edrecolomab targets the 17-1 A antigen seen in colon and rectal cancer, and has been approved for use in Europe for these indications. Its antitumor effects are mediated through ADCC, CDC, and the induction of an anti-idiotypic network. Trastuzumab targets the HER-2/neu antigen. This antigen is seen on 25% to 35% of breast cancers. Trastuzumab is thought to work in a variety of ways: downregulation of HER-2 receptor expression, inhibition of proliferation of human tumor cells that overexpress HER-2 protein, enhancing immune recruitment and ADCC against tumor cells that overexpress HER-2 protein, and downregulation of angiogenesis factors. Alemtuzumab (Campath) is used in the treatment of chronic lymphocytic leukemia; colon cancer and lung cancer; Gemtuzumab (Mylotarg) finds use in the treatment of acute myelogenous leukemia; Ibritumomab (Zevalin) finds use in the treatment of non-Hodgkin's lymphoma; Panitumumab (Vectibix) finds use in the treatment of colon cancer. Cetuximab (Erbitux) is also of interest for use in the methods of the invention. The antibody binds to the EGF receptor (EGFR), and has been used in the treatment of solid tumors including colon cancer and squamous cell carcinoma of the head and neck (SCCHN).

Pharmaceutical Compositions

An aspect of the present invention relates to a pharmaceutical composition comprising the antibody of the invention.

Typically, the antibody of the present invention is administered to the subject in the form of a pharmaceutical composition which comprises a pharmaceutically acceptable carrier. Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. For use in administration to a patient, the composition will be formulated for administration to the patient. The compositions of the present invention may be administered orally, parenterally, by inhalation spray, topically, rectally, nasally, buccally, vaginally or via an implanted reservoir. The used herein includes subcutaneous, intravenous, intramuscular, intra-articular, intra-synovial, intrasternal, intrathecal, intrahepatic, intralesional and intracranial injection or infusion techniques. Sterile injectable forms of the compositions of this invention may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. The compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include, e.g., lactose. When aqueous suspensions are required for oral use, the active ingredient is combined with emulsifying and suspending agents. If desired, certain sweetening, flavoring or coloring agents may also be added. Alternatively, the compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols. The compositions of this invention may also be administered topically, especially when the target of treatment includes areas or organs readily accessible by topical application, including diseases of the eye, the skin, or the lower intestinal tract. Suitable topical formulations are readily prepared for each of these areas or organs. For topical applications, the compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water. Topical application for the lower intestinal tract can be effected in a rectal suppository formulation (see above) or in a suitable enema formulation. Patches may also be used. The compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents. For example, an antibody present in a pharmaceutical composition of this invention can be supplied at a concentration of 10 mg/mL in either 100 mg (10 mL) or 500 mg (50 mL) single-use vials. The product is formulated for IV administration in 9.0 mg/mL sodium chloride, 7.35 mg/mL sodium citrate dihydrate, 0.7 mg/mL polysorbate 80, and Sterile Water for Injection. The pH is adjusted to 6.5. An exemplary suitable dosage range for an antibody in a pharmaceutical composition of this invention may between about 1 mg/m2 and 500 mg/m2. However, it will be appreciated that these schedules are exemplary and that an optimal schedule and regimen can be adapted taking into account the affinity and tolerability of the particular antibody in the pharmaceutical composition that must be determined in clinical trials. A pharmaceutical composition of the invention for injection (e.g., intramuscular, i.v.) could be prepared to contain sterile buffered water (e.g. 1 ml for intramuscular), and between about 1 ng to about 100 mg, e.g. about 50 ng to about 30 mg or more preferably, about 5 mg to about 25 mg, of an anti-myosin 18A antibody of the invention.

In certain embodiments, the use of liposomes and/or nanoparticles is contemplated for the introduction of antibodies into host cells. The formation and use of liposomes and/or nanoparticles are known to those of skill in the art.

Nanocapsules can generally entrap compounds in a stable and reproducible way. To avoid side effects due to intracellular polymeric overloading, such ultrafine particles (sized around 0.1 µm) are generally designed using polymers able to be degraded in vivo. Biodegradable polyalkyl-cyanoacrylate nanoparticles that meet these requirements are contemplated for use in the present invention, and such particles may be are easily made.

Liposomes are formed from phospholipids that are dispersed in an aqueous medium and spontaneously form multilamellar concentric bilayer vesicles (also termed multilamellar vesicles (MLVs)). MLVs generally have diameters of from 25 nm to 4 µm. Sonication of MLVs results in the formation of small unilamellar vesicles (SUVs) with diameters in the range of 200 to 500 Å, containing an aqueous solution in the core. The physical characteristics of liposomes depend on pH, ionic strength and the presence of divalent cations.

Kits

Finally, the invention also provides kits comprising at least one antibody of the invention. Kits containing antibodies of the invention find use in detecting sideroflexin-3 expression (increase or decrease), or in therapeutic or diagnostic assays. Kits of the invention can contain an antibody coupled to a solid support, e.g., a tissue culture plate or beads (e.g., sepharose beads). Kits can be provided which contain antibodies for detection and quantification of sideroflexin-3 in vitro, e.g. in an ELISA or a Western blot or flow cytometry. Such antibody useful for detection may be provided with a label such as a fluorescent or radiolabel.

The invention will be further illustrated by the following figures and examples. However, these examples and figures should not be interpreted in any way as limiting the scope of the present invention.

FIGURES

FIG. 1. High staining of NLC by the four anti-NLC antibodies. A. Staining with the four anti-NLC antibodies of B-CLL and NLC gated from a patient with CLL and of monocytes, T cells and B cells from blood sample of an healthy donor (full line: isotype control; dashed line: antibodies). B. Positive staining with the 6-25 antibody on gated CD163$^+$ NLC and negative staining on other cells. C. Mean of the fluorescence intensity of the four antibodies staining on NLC gated compared to that of the isotype control.

Figure 2:
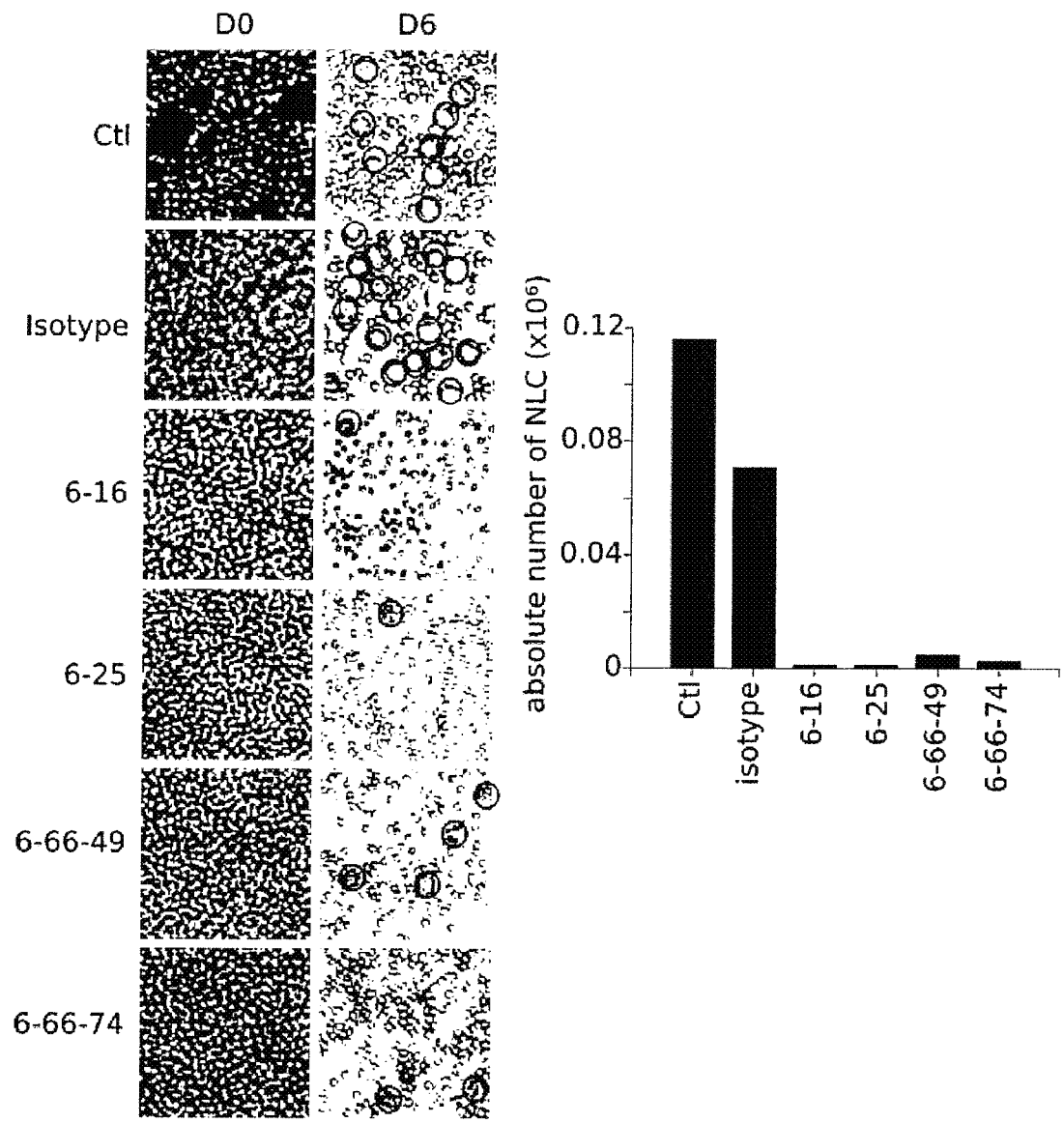

FIG. 2. NLC depletion and leukemic cells death when cultured with the 4 antibodies. Visualisation by microscopy of the depletion of NLC (surrounded) in a culture of PBMC from a patient with CLL after 6 days in the presence of each anti-NLC antibodies compared to the isotype condition. The absolute number of NLC in these cultures was near to zero in the conditions with each antibody.

Figure 3:
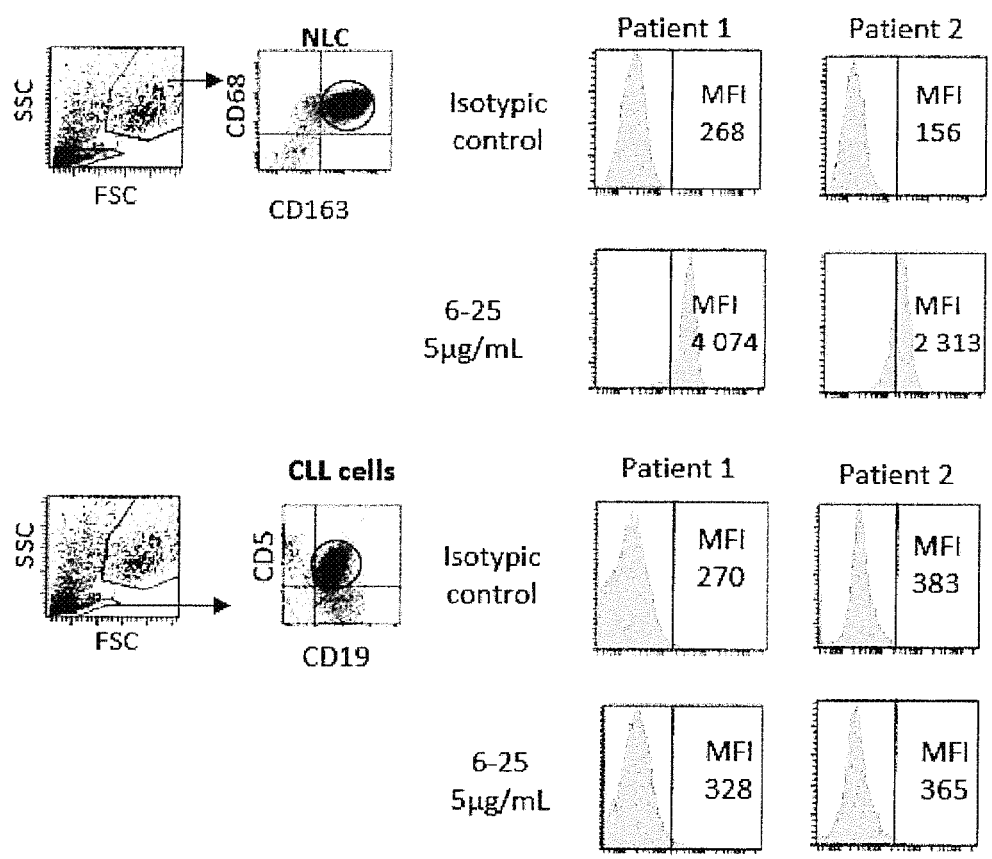

FIG. 3: Staining of PBMC from 2 CLL patients after 10 days of culture, with the 6-25 antibody or the isotypic control and FACS analysis. (MFI: mean fluorescence intensity).

Figure 4:
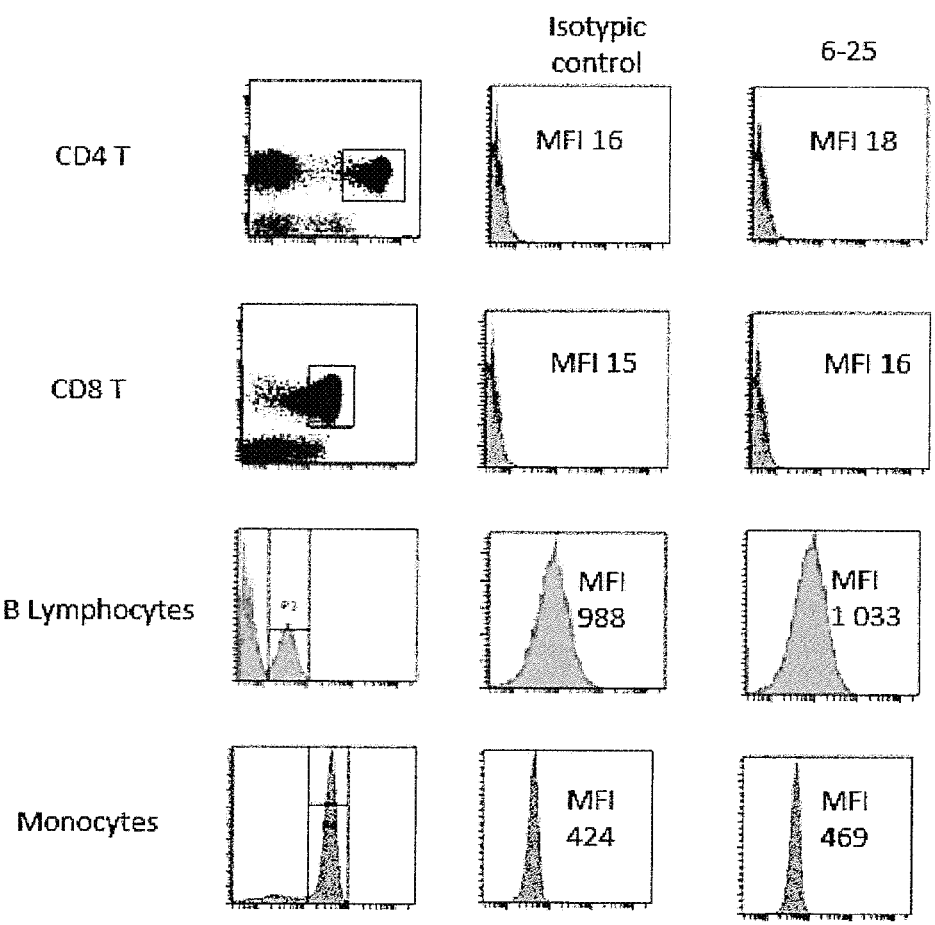

FIG. 4: Staining of PBMC from healthy donor with the 6-25 antibody or the isotypic control and FACS analysis. (MFI: mean fluorescence intensity).

Figure 5:
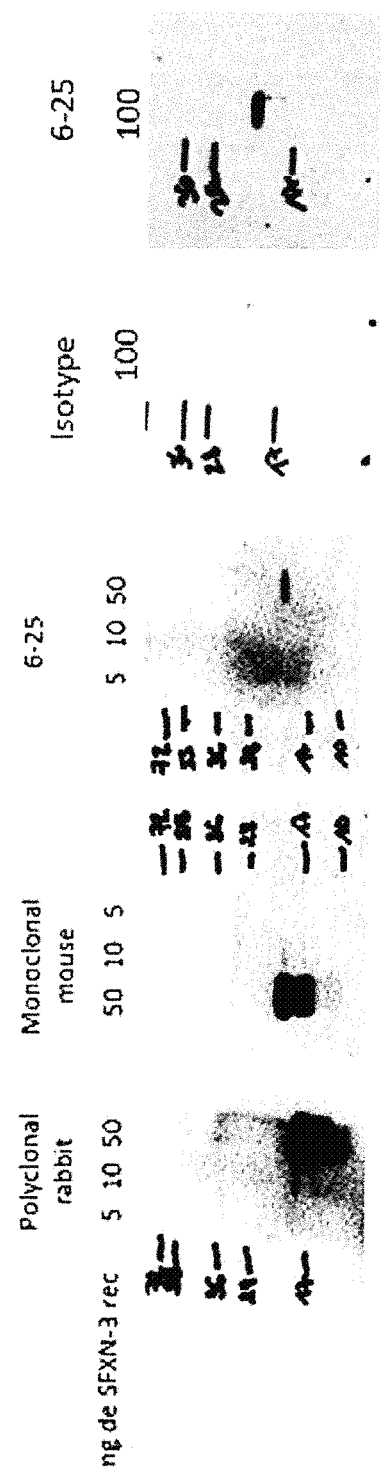

FIG. 5: Western blot of the recombinant sideroflexin 3 revealed by two commercial anti-SFXN3 antibodies and the 6-25 antibody or the isotype.

Figure 6:
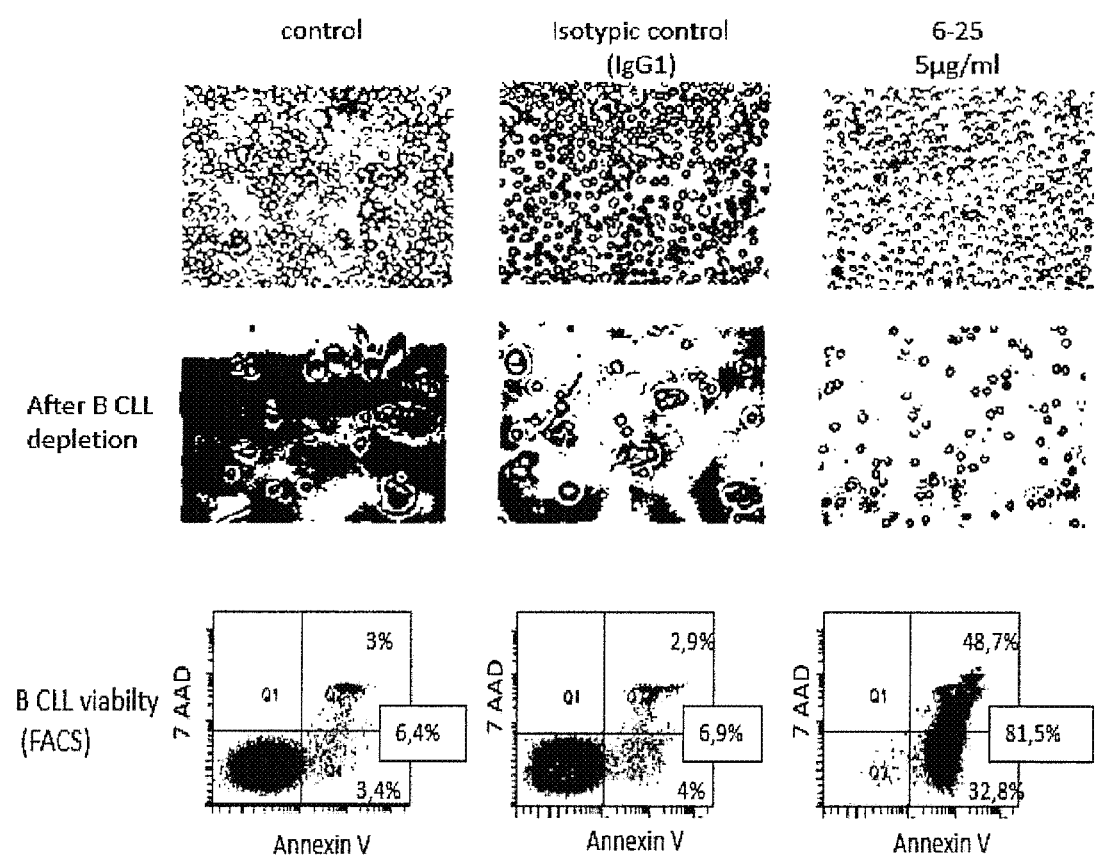

FIG. 6: Microscopy and B CLL viability analysis, from a 10 days culture of PBMC from CLL patient with or without 6-25 antibody or isotypic control. FACS: Percentage of dead B CCL framed.

Figure 7:
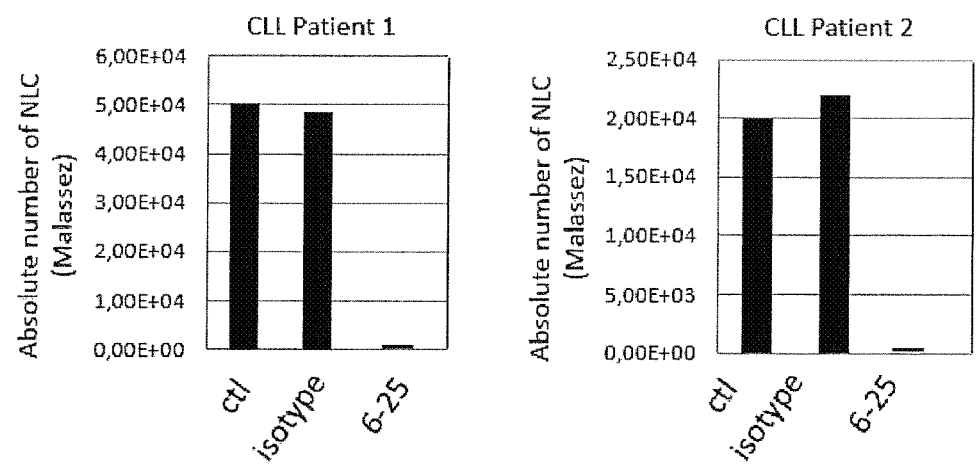

FIG. 7: NLC numbers after 10 days of culture of CLL patient's PBMC with or without 6-25 or isotypic control.

EXAMPLE 1: SIDEROFLEXIN TO TARGET TUMOR ASSOCIATED MACROPHAGES

Material & Methods

PBMC from patients were isolated using Ficoll and cultured 10 days at 10 $10^6$ cells/ml in RPMI 10% FBS. Then supernatant were removed and adherents cells (NLC) were washed twice with PBS. NLC were detached using cell scraper, counted and dried pellets were freezed. Dry pellets of non adherent cells were also freezed. NLC from several patients were pooled and membrane proteins were extracted using the "Proteo-extract native membrane protein extraction kit" (Calbiochem).

Pierce™ High Capacity Streptavidin Agarose beads (thermo Fisher Scientific) were incubated with goat anti mouse IgG-biotin (Sigma Aldrich, B7401) 20 minutes at room temperature, washed three times and then incubated 2 hours at 4° C. with hybridoma's supernatant culture medium or with a control medium. After three PBS washes, coated beads were incubated over night at 4° C. with 500 µg of membrane proteins from NLC or non-adherent cells. Beads were washed and eluted with Laemmli solution. These solutions were loaded in an acrylamide gel and colored with instant blue (euromedex) after migration. Gel strips were cut and peptides were extracted. Briefly, strips were washed with acetonitrile and ammonium bicarbonate, reduced and alkylated with DTT and iodoacetamin, digested with trypsin and then peptides were extracted with acetonitrile and formic acid. Peptides were then identified by mass spectometry. Identified peptides in each condition (without hybridoma's supernatant, without proteins, with proteins from non-adherent cells and from NLC) were compared.

Results

To determine the target of the four antibodies which specifically recognize NLC, we tested by immunoprecitation the four hybridomas culture supernatants. We thus identified by mass spectrometry the peptides associated to each hybridomas.

We found these peptides:
6-16: sideroflexin 3 and GRP78
6-25: sideroflexin 3
6-66-49: GRP78
6-66-74: endoplasmine and GRP78

EXAMPLE 2: TARGETING OF TUMOR ASSOCIATED MACROPHAGES

Material & Methods

Production of Antibodies Against NLC

NLC were generated from culture of PBMC isolated from blood samples of patients with chronic lymphoid leukemia (CLL) at 10 $10^6$ cells/ml in RPMI 10% FBS. After 14 days of culture at 37° C. and in a 5% $CO_2$ atmosphere, B leukemic cells were removed and adherent cells (NLC) were collected. Between 3 and 15 millions of NLC from different donors were injected to mouse in intraperitoneal four times every 15 days. Splenocytes were then isolated from the spleen and fusion with the α63s2 murine myeloma cell line produced 200 hybridomas. The 200 conditioned medium of these hybridomas cultures were incubated with NLC or leukemic cells for 30 minutes at 4° C., then with a fluorescent secondary anti-mouse antibody. These cells were then analyzed by flow cytometry.

Flow Cytometry Analysis

50 µl of each hybridoma culture supernatant were incubated with 0.2 millions of cells (NLC, B leukemic cells or PBMC from CLL' patients or healthy donors) for 30 minutes at 4° C. After washing with PBS, cells were incubated with goat anti-mouse antibody coupled to a fluorochrome for 30 minutes at 4° C. After washing, cells were incubated with antihuman-CD163, antihuman-CD3, antihuman-CD19 and antihuman-CD14 coupled to different fluorochromes for 15 minutes at 4° C. After washing, cells were analyzed by flow cytometry.

Culture with Antibodies

PBMC isolated from a patient with CLL were cultured for 6 days with or without 5 µl/ml of purified antibodies from hybridomas culture supernatants or with 5 µg/ml of isotype control. Numbers of NLC were then estimated by a counting under microspcope and viable leukemic cells were evaluated thanks to a cell counter using propidium iodure for the viability.

Immunohistochemistry

IHC was performed on 4-µm-thick routinely processed formalin-fixed paraffin-embedded sections of tumor specimens with neighboring normal tissue. A heat-induced epitope retrieval technique in a citrate buffer (pH 6) was performed. Each antibody was incubated for 30 min and revealed using EnVision G|2 System/AP (Dako) enzyme-conjugated polymer backbone according to the manufacturer's protocol and visualized by Permanent Red Chromogen (Fas Red) included in the kit. The µm-thick sections were stained with hematoxylin and eosin (H&E). The IHC was processed using an Autostainer plus (Dako) slide processor.

Results

Flow Cytometry Analysis of 4 Specific Antibodies to NLC.

NLC were described as the Tumor Associated Macrophages (TAM) of CLL.

To target NLC, we decided to produce a specific antibody against NLC. Thus, we immunized mouse with purified NLC from patients with LLC. NLC were generated by the in vitro culture of Peripheral Blood Mononuclear Cells (PBMC) from patients. After 14 days, NLC were isolated then injected to mouse. About 200 hybridomas were obtained and their supernatants were tested in flow cytometry for their capability to recognize NLC from patients. Among these 200 supernatants, 4 (6-16, 6-25, 6-66-49, 6-66-74) recognized and fixed NLC, but not leukemic cells and very few monocytes from patient with LLC. FIG. 1A shows the staining with each supernatant in blue compared to the yellow isotype. These supernatants did not fixed T ($CD3^+$) or B ($CD19^+$) lymphocytes from healthy donors (FIG. 1 A). FIG. 1B shows the double staining of NLC with CD163, specific antibody to TAM/NLC, and 6-25 antibody, while other PBMC were not recognized by these two antibodies. These supernatants contain thus specific antibodies for NLC which isotype was determined as IgG1. The mean fluorescence intensity of the 4 antibodies is represented in FIG. 1C compared to that of isoptype.

Antibodies Functionality

To test the antibodies functionality, we cultured PBMC from a patient with CLL with each of the 4 antibodies and showed at 6 days of culture a strong decrease of NLC number (big cells surrounded) and a decrease of the number of viable B leukemic cells compared to the culture without antibody or with isotype control (FIG. 2).

Detection of TAM in Breast Tumor

To test if the 4 antibodies were able to recognize other TAM than NLC in CLL, we performed staining in IHC of a breast tumor with the 4 antibodies. We showed that in pH6 condition, 2 of these antibodies, 6-25 and 6-66-49, produced a specific brown staining on macrophages and preferentially in the edge of the tumor, characteristic of an inflammatory area, and inside the tumor. However, a very low staining were detected away from the tumor namely in "healthy" tissue. Moreover, cancer cells or other immune cells were not stained in brown.

EXAMPLE 3

Material & Methods

Staining of NLC and CLL Cells with the 6-25 Antibody by Flow Cytometry Analysis

PBMC isolated from blood samples of 2 CLL patients were cultured for 10 days. PBMC were then stained for 30 minutes at 4° C. with the 6-25 antibody or the appropriate isotypic control. After washing with PBS, cells were incubated with goat anti-mouse antibody coupled to a fluorochrome for 30 minutes at 4° C. After washing, cells were incubated with antihuman-CD163, antihuman-CD68, antihuman-CD5 and antihuman-CD19 coupled to different fluorochromes for 15 minutes at 4° C. After washing, cells were analyzed by flow cytometry. NLC were selected by the positive staining for CD163/CD68 and CLL cells were selected by the positive staining for CD19/CD5.

Staining of PBMC from Healthy Donor with the 6-25 Antibody by Flow Cytometry Analysis PBMC isolated from a buffy coat of an healthy donor were stained for 30 minutes at 4° C. with the 6-25 antibody or the appropriate isotypic control. After washing with PBS, cells were incubated with goat anti-mouse antibody coupled to a fluorochrome for 30 minutes at 4° C. After washing, cells were incubated with antihuman-CD3 antihuman-CD4, antihuman-CD8, antihuman-CD14 and antihuman-CD19 coupled to different fluorochromes for 15 minutes at 4° C. After washing, cells were analyzed by flow cytometry. Each populations were selected by their specific marker (CD3+/CD4+ for CD4 T cells, CD3+/CD8+ for CD8 T cells, CD3−/CD19+ for B lymphocytes, CD3−/CD14+ for monocytes).

Viability of B CLL Cells and NLC after Culture with the 6-25 Antibody

PBMC isolated from blood sample of a patient with CLL were cultured for 6 days with or without 5 µg/ml of purified 6-25 antibody or with 5 µg/ml of isotype control (murine IgG1). Photography were obtained on a phase contrast microscope (×20) before and after depletion of B CLL. NLC were counted on the Malassez lamella. Viable leukemic cells were evaluated thanks to a staining with 7AAD and annexin V then a FACS analysis.

Western Blot 5, 10, 50 or 100 ng of recombinant sideroflexin 3 were subjected to western blotting and probed overnight at 4° C. with 10 μg/ml antibody solution with: a rabbit polyclonal anti-SFXN3 or a mouse monoclonal anti-SFXN3 or the 6-25 antibody or a mouse IgG1 isotype. After washing, membranes were incubated 1 h at room temperature with a solution of secondary antibody (1/10000, HRP). Revelation was then made with ECL.

Results

NLC (CD68+CD163+ cells) generated from the culture for 10 days of PBMC from two CLL patients were stained by the 6-25 antibody compared to the isotypic control. However, CLL cells gated (CD5+CD19+) from the same cultures were not stained by the 6-25 antibody, similar mean fluorescence intensities were obtained for CLL cells with the 6-25 and with the isotypic control (FIG. 3).

PBMC from healthy donor were incubated with the 6-25 antibody or the isotypic control and neither the CD4 T cells, nor the CD8 T cells, nor the B lymphocytes nor the monocytes were stained with the 6-25 antibody. For each population gated, Mean fluorescence intensity obtained with 6-25 was similar to that obtained with the isotypic control (FIG. 4).

Human recombinant sideroflexin 3 was recognized in western blot by the 6-25 antibody with a band corresponding to a size of 22 kDa. Recognition of this human recombinant sideroflexin 3 was checked by western blot with two commercial antibodies, a rabbit polyclonal and a mouse monoclonal antibodies. Two bands were obtained with these two antibodies, one of which corresponded to the size of the sideroflexin 3 (22 kDa) (FIG. 5).

To analyze the functionality of the 6-25 antibody, we cultured PBMC of a CLL patient with or without 6-25 or isotypic control for 6 days. After 6 days, depletion of NLC was showed in the culture with 6-25. The depletion was more evident after elimination of B CCL. NLC development were not affected in the culture with the isotypic control or without antibody. Round and adherent cells was indeed visualized in these cultures compared to that with the 6-25 antibody. Then, viability of B CLL cells was analyzed in these three culture with a staining with anexin V and 7-AAD and FACS analysis. Viability of B CLL was high after 6 days of culture with or without the isotypic control, only 6.4% of dead cells. However, 81.5% of B CLL were dead after 6 days of culture in the presence of the 6-25 antibody (FIG. 6).

NLC were also counted in cultures of PBMC from two CLL patients with or without 6-25 or isotypic control. NLC number was close to zero in the culture with 6-25 compared to cultures with or without the isotypic control (FIG. 7).

REFERENCES

Throughout this application, various references describe the state of the art to which this invention pertains. The disclosures of these references are hereby incorporated by reference into the present disclosure.

The invention claimed is:

1. An antibody wherein said antibody comprises:
   (a) a heavy chain wherein the variable domain comprises:
      a H-CDR1 having the sequence set forth as SEQ ID NO: 1, and
      a H-CDR2 having the sequence set forth as SEQ ID NO: 2, and
      a H-CDR3 having the sequence set forth as SEQ ID NO: 3;
   and
   (b) a light chain wherein the variable domain comprises:
      a L-CDR1 having the sequence set forth as SEQ ID NO: 4, and
      a L-CDR2 having the sequence set forth as SEQ ID NO: 5, and a L-CDR3 having the sequence set forth as SEQ ID NO: 6.

2. The antibody according to claim 1 wherein said antibody comprises:
a heavy chain wherein the variable domain has at least 70% identity with the sequence set forth as SEQ ID NO: 7, and
a light chain wherein the variable domain has at least 70% identity with the sequence set forth as SEQ ID NO: 8.

3. The antibody according to claim 1 wherein said antibody comprises:
a heavy chain wherein the variable domain has the sequence set forth as SEQ ID NO: 7 and
a light chain wherein the variable domain has the sequence set forth as SEQ ID NO: 8.

4. The antibody according to claim 1, wherein said antibody depletes Tumor Associated Macrophages.

5. The antibody according to claim 1, which is a chimeric antibody or a humanized antibody.

6. A nucleic acid molecule encoding the antibody of claim 1.

7. A nucleic acid molecule which encodes for the heavy chain and the light chain of the antibody of claim 1.

8. The nucleic acid molecule of claim 6 which comprises a nucleic acid sequence having at least 70% identity with SEQ ID NO:9 and SEQ ID NO:10.

9. A vector comprising the nucleic acid molecule according to claim 6.

10. A host cell which has been transfected, infected or transformed by i) the nucleic acid according to claim 7 and/or ii) a vector comprising the nucleic acid according to claim 6.

11. A method for detecting Tumor Associated Macrophages, and/or for measuring an amount of Tumor Associated Macrophages in a biological sample, comprising contacting said biological sample with the antibody of claim 1.

12. A method of treating a cancer associated with Tumor Associated Macrophage in a subject in need thereof, comprising administering to the subject a therapeutically effective amount of the antibody of claim 1.

13. A pharmaceutical composition comprising the antibody of claim 1.

14. The antibody of claim 1, wherein the antibody binds to sideroflexin-3.

15. The method of claim 12, wherein the cancer associated with Tumor Associated Macrophage is a solid tumor or a leukemia.

16. A host cell comprising
i) a nucleic acid encoding a heavy chain wherein the variable domain comprises:
a H-CDR1 having the sequence set forth as SEQ ID NO: 1, and
a H-CDR2 having the sequence set forth as SEQ ID NO: 2, and
a H-CDR3 having the sequence set forth as SEQ ID NO: 3;
and
ii) a nucleic acid encoding a light chain wherein the variable domain comprises:
a L-CDR1 having the sequence set forth as SEQ ID NO: 4, and
a L-CDR2 having the sequence set forth as SEQ ID NO: 5, and
a L-CDR3 having the sequence set forth as SEQ ID NO: 6.

17. A host cell which has been transfected, infected or transformed by
i) a vector comprising a nucleic acid encoding a heavy chain wherein the variable domain comprises:
a H-CDR1 having the sequence set forth as SEQ ID NO: 1, and
a H-CDR2 having the sequence set forth as SEQ ID NO: 2, and
a H-CDR3 having the sequence set forth as SEQ ID NO: 3;
and
ii) a vector comprising a nucleic acid encoding a light chain wherein the variable domain comprises:
a L-CDR1 having the sequence set forth as SEQ ID NO: 4, and
a L-CDR2 having the sequence set forth as SEQ ID NO: 5, and
a L-CDR3 having the sequence set forth as SEQ ID NO: 6.

* * * * *